(12) United States Patent
Zhadkevich

(10) Patent No.: US 10,195,402 B2
(45) Date of Patent: Feb. 5, 2019

(54) CAROTID ARTERY OCCLUDING APPARATUS WITH FIRST AND SECOND OCCLUDING BALLOONS

(71) Applicant: Michael Zhadkevich, Greenwood, SC (US)

(72) Inventor: Michael Zhadkevich, Greenwood, SC (US)

(*) Notice: Subject to any disclaimer, the term of this patent is extended or adjusted under 35 U.S.C. 154(b) by 129 days.

(21) Appl. No.: 15/431,814

(22) Filed: Feb. 14, 2017

(65) Prior Publication Data
US 2017/0165457 A1 Jun. 15, 2017

Related U.S. Application Data

(62) Division of application No. 13/941,756, filed on Jul. 15, 2013, now Pat. No. 9,597,084.
(Continued)

(51) Int. Cl.
*A61M 29/00* (2006.01)
*A61M 25/10* (2013.01)
(Continued)

(52) U.S. Cl.
CPC ......... *A61M 25/10* (2013.01); *A61B 5/02158* (2013.01); *A61B 17/1204* (2013.01);
(Continued)

(58) Field of Classification Search
CPC .......... A61B 17/12031; A61B 17/1204; A61B 17/12045; A61B 17/12109;
(Continued)

(56) References Cited

U.S. PATENT DOCUMENTS

| 3,587,584 A | 6/1971 | Bourbon |
| 4,395,806 A | 8/1983 | Wonder |

(Continued)

FOREIGN PATENT DOCUMENTS

| EP | 0 203 310 A2 | 3/1986 |
| EP | 2 260 776 A1 | 12/2010 |

(Continued)

OTHER PUBLICATIONS

Wikipedia; "Pulmonary artery catheter Pulmonary artery catheter", Wikipedia, The Free Encyclopedia., May 12, 2012, XP055235920, Retrieved from the Internet:URLhttps://en.wikipedia.org/w/index. php?title=Pulmonary_artery_catheter&oldid+694424669 [retrieved on Dec. 14, 2015] (copy in parent application).

(Continued)

*Primary Examiner* — Elizabeth Houston
*Assistant Examiner* — Mohamed Gabr
(74) *Attorney, Agent, or Firm* — J. Bennett Mullinax, LLC

(57) ABSTRACT

An apparatus for preventing stroke by occluding blood flow through a right carotid artery and a left carotid artery of a patient is provided. The apparatus has a first occluding catheter that carries a first occluding balloon that has an inflated configuration that occludes either the right carotid artery or the left carotid artery. The apparatus also includes a second occluding catheter that carries a second occluding balloon that has an inflated configuration that occludes the other one of the right carotid artery or the left carotid artery that is not occluded by the first occluding balloon. An insertion device may also be present to allow for insertion of the first and second occluding catheters.

14 Claims, 15 Drawing Sheets

Related U.S. Application Data

(60) Provisional application No. 61/672,706, filed on Jul. 17, 2012.

(51) Int. Cl.

| | | |
|---|---|---|
| *A61B 17/12* | (2006.01) | |
| *A61B 5/0215* | (2006.01) | |
| *A61M 25/00* | (2006.01) | |
| *A61B 5/00* | (2006.01) | |
| *A61M 25/06* | (2006.01) | |
| *A61B 17/22* | (2006.01) | |
| *A61B 17/00* | (2006.01) | |

(52) U.S. Cl.
CPC .. *A61B 17/12031* (2013.01); *A61B 17/12036* (2013.01); *A61B 17/12045* (2013.01); *A61B 17/12109* (2013.01); *A61B 17/12136* (2013.01); *A61M 25/003* (2013.01); *A61M 25/104* (2013.01); *A61M 25/1011* (2013.01); *A61B 5/6853* (2013.01); *A61B 2017/00106* (2013.01); *A61B 2017/00119* (2013.01); *A61B 2017/00132* (2013.01); *A61B 2017/1205* (2013.01); *A61B 2017/12127* (2013.01); *A61B 2017/22067* (2013.01); *A61M 25/0032* (2013.01); *A61M 2025/0003* (2013.01); *A61M 2025/0037* (2013.01); *A61M 2025/0681* (2013.01); *A61M 2025/1045* (2013.01); *A61M 2025/1052* (2013.01)

(58) Field of Classification Search
CPC ...... A61B 17/12136; A61B 2017/1205; A61B 2017/12127; A61B 5/02158; A61B 5/6853; A61M 2025/0003; A61M 2025/0037; A61M 2025/0681; A61M 2025/1052; A61M 25/003; A61M 25/0031; A61M 25/104
See application file for complete search history.

(56) References Cited

U.S. PATENT DOCUMENTS

| | | | |
|---|---|---|---|
| 4,676,232 | A | 6/1987 | Olsson et al. |
| 4,745,924 | A | 5/1988 | Ruff |
| 4,984,563 | A | 1/1991 | Renaud |
| 5,059,177 | A | 10/1991 | Towne |
| 5,271,409 | A | 12/1993 | Millay |
| 5,360,403 | A | 11/1994 | Mische |
| 5,441,051 | A | 8/1995 | Hileman |
| 5,514,079 | A | 5/1996 | Dillon |
| 5,741,295 | A | 4/1998 | McEwen |
| 6,156,005 | A | 12/2000 | Theron |
| 6,168,579 | B1 | 1/2001 | Tsugita |
| 6,426,916 | B2 | 7/2002 | Garrison et al. |
| 6,595,980 | B1 | 7/2003 | Barbut |
| 7,458,980 | B2 | 12/2008 | Barbut |
| 7,727,254 | B2 | 6/2010 | Pah |
| 7,972,356 | B2 | 7/2011 | Boyle et al. |
| D643,536 | S | 8/2011 | Vivenzio |
| 7,998,104 | B2 | 8/2011 | Chang |
| 8,025,674 | B2 | 9/2011 | Barbut et al. |
| 8,034,043 | B1 | 10/2011 | Barbut |
| 8,062,324 | B2 | 11/2011 | Shimon et al. |
| 2002/0115982 | A1 | 8/2002 | Barbut et al. |
| 2002/0173815 | A1 | 11/2002 | Hogendijk |
| 2003/0036728 | A1 | 2/2003 | Samson |
| 2003/0176884 | A1 | 9/2003 | Berrada |
| 2005/0015048 | A1 | 1/2005 | Chiu |
| 2005/0059931 | A1* | 3/2005 | Garrison ............... A61M 25/10 604/101.04 |
| 2005/0075531 | A1 | 4/2005 | Loeb et al. |
| 2005/0154344 | A1* | 7/2005 | Chang ............. A61B 17/12136 604/6.09 |
| 2005/0197624 | A1 | 9/2005 | Goodson |
| 2009/0326575 | A1 | 12/2009 | Galdonik |
| 2010/0179583 | A1 | 7/2010 | Carpenter et al. |
| 2010/0324589 | A1 | 12/2010 | Carpenter et al. |
| 2011/0028934 | A1 | 2/2011 | Buckman et al. |
| 2011/0054322 | A1 | 3/2011 | Zanatta |
| 2012/0179195 | A1 | 7/2012 | Lashinski |
| 2012/0203265 | A1* | 8/2012 | Heuser ..................... A61F 2/01 606/200 |
| 2013/0023909 | A1 | 1/2013 | Duhay |
| 2014/0336690 | A1 | 11/2014 | Zhadkevich |

FOREIGN PATENT DOCUMENTS

| | | |
|---|---|---|
| EP | 2 682 154 A1 | 1/2014 |
| WO | WO 99/36028 | 7/1999 |
| WO | WO 00/32266 A1 | 6/2000 |
| WO | WO 01/13983 A2 | 3/2001 |
| WO | WO 2010/081025 A1 | 7/2010 |
| WO | WO 2011/017103 A2 | 2/2011 |
| WO | WO 2012/083227 A1 | 6/2012 |

OTHER PUBLICATIONS

Extended European Search Report and Written Opinion of the European Patent Office; European Application No. 13176708.9-1654/2687167; European Patent Office, Munich, Germany; Dec. 22, 2015; copyright 2015 European Patent Office; copy in parent application; (21 pages).

European Patent Office; European Search Report; European Application No. 16178698.3-1654; dated Nov. 18, 2016; pp. 1-9; copyright 2016 European Patent Office; Munich, Germany; copy in parent application; (9 pages).

European Patent Office; European Search Report; European Application No. 16178617.3-1654; dated Nov. 16, 2016; pp. 1-5; copyright 2016 European Patent Office; Munich, Germany; copy in parent application; (5 pages).

European Patnt Office; European Search Report; European Application No. 16178609.0-1654; dated Nov. 21, 2016; pp. 1-9; copyright 2016 European Patent Office; Munich, Germany; copy in parent application; (9 pages).

Joe Elbery; "Swan Ganz Physiology"; You Tube video retrieved from https://www.youtube.com/watch?v=7putxZN7ij4; Jan. 21, 2012; copyright 2012; published by Edwards Lifesciences, Irvine, California, USA; (2 page screen shot copy in parent application).

Various Anonymous Authors; "Circle of Willis"; Wikipedia article retrieved from https://en.wikipedia.org/wiki/Circle_of_Willis; retrieved on Nov. 8, 2016; pp. 1-4; copyright 2016 Wikipedia Foundation Inc.; San Francisco; California; USA; copy in parent application (4 pages).

European Patent Office; Extended European Search Report; European Application No. 14166170.2-1654; European Patent Office; pp. 1-7, publisher European Patent Office; Published Munich, Germany; copyright and dated Jul. 28, 2014, copy in parent application; (7 pages).

United States Patent Office, Office Action; U.S. Appl. No. 15/333,076; United States Patent Office; pp. 1-15, publisher United States Patent Office; Published Alexandria, Virginia, USA; copyright and dated Sep. 5, 2018; (15 pages).

* cited by examiner

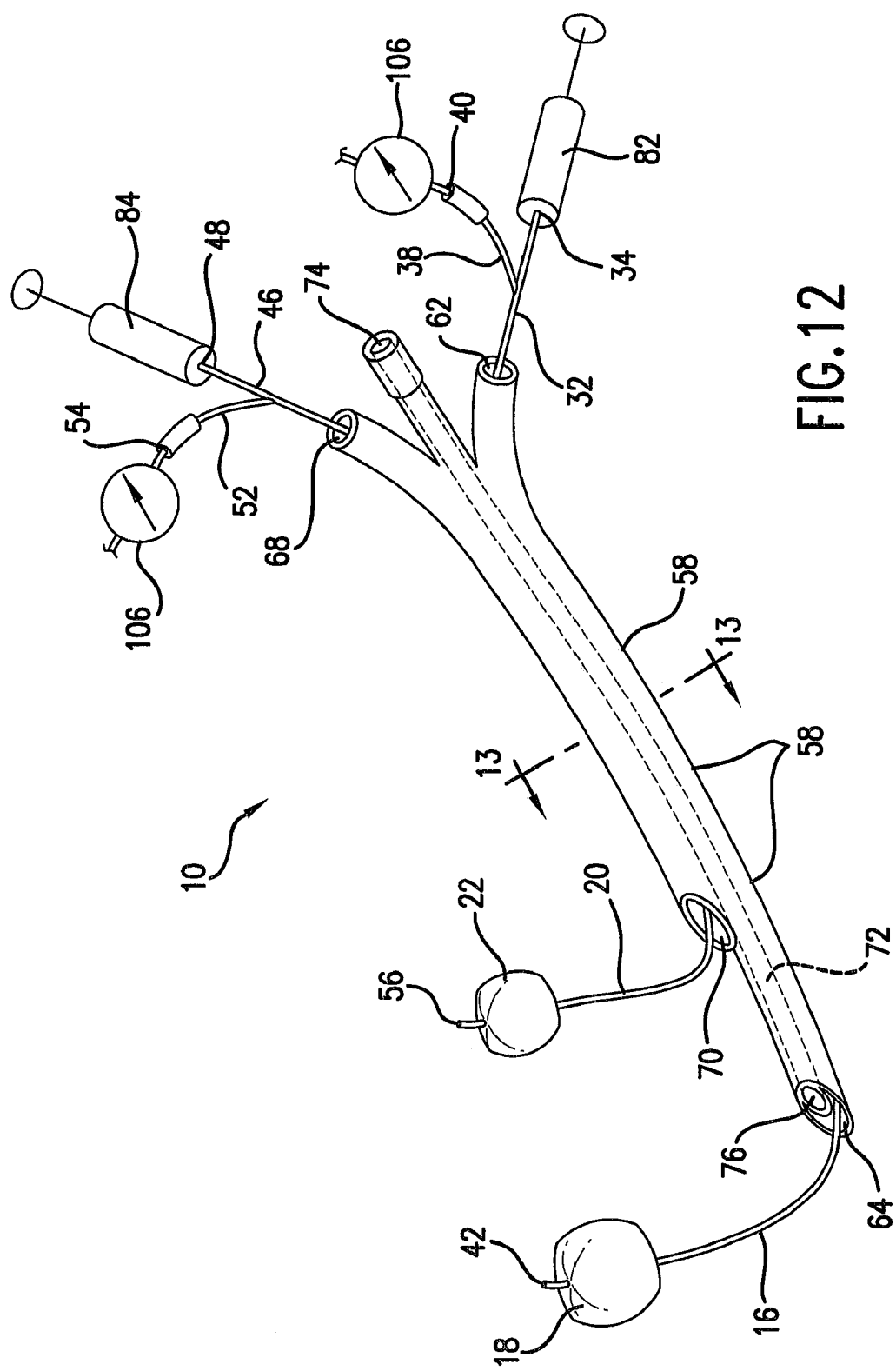

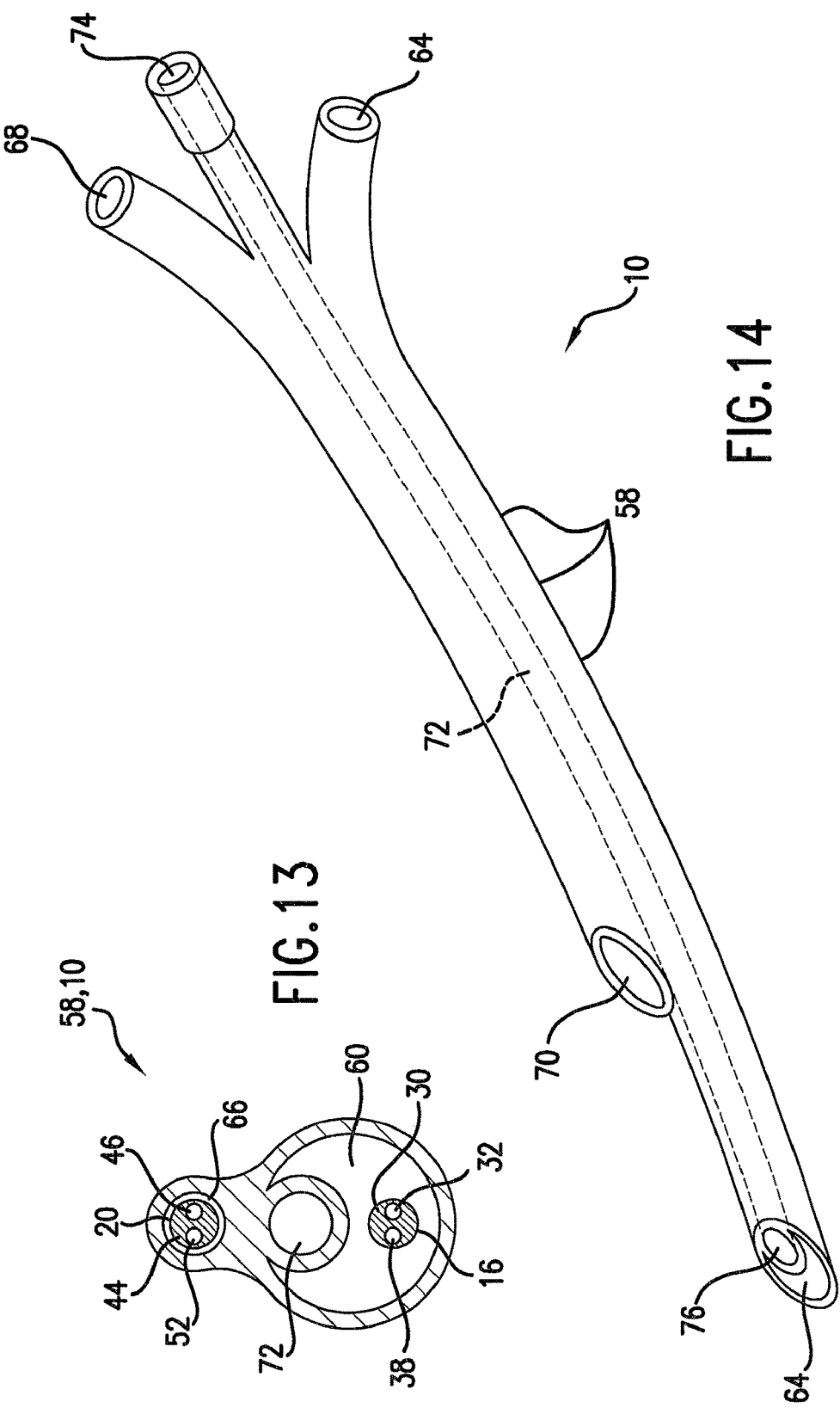

CAROTID ARTERY OCCLUDING APPARATUS WITH FIRST AND SECOND OCCLUDING BALLOONS

CROSS REFERENCE TO RELATED APPLICATIONS

This application is a divisional application of and claims the benefit of U.S. application Ser. No. 13/941,756 filed on Jul. 15, 2013 and entitled "Carotid Artery Occluding Apparatus with First and Second Occluding Balloons." U.S. application Ser. No. 13/941,756 claims the benefit of U.S. Application Ser. No. 61/672,706 filed on Jul. 17, 2012 and entitled, "Endovascular Device and Method of Prevention of Embolic Stroke." U.S. Application Ser. No. 61/672,706 and U.S. application Ser. No. 13/941,756 are both incorporated by reference herein in their its entirety for all purposes.

FIELD OF THE INVENTION

The present invention relates generally to devices and methods for the prevention of stroke. More particularly, the present application involves an apparatus that has two occluding balloons that are inserted into the circulatory system of the patient to block blood flow, and hence emboli, through the carotid arteries and if needed subclavian arteries, during performance of an emboligenic procedure to prevent emboli from passing, through the carotid arteries and potentially vertebral arteries and causing stroke.

BACKGROUND

Intraoperative embolic stroke is one of the most dreadful complications of cardiac, aortic and vascular procedures, diagnosed in 1-22% of patients undergoing cardiovascular surgery. Even more frequently, in up to 70% of cases, patients undergoing heart, valve, coronary artery bypass and aortic surgery experience subclinical embolic events as recorded by transcranial Doppler and MRI. These embolic events lead to cognitive impairment and disability and have a significant impact on patients' recovery.

The main sources of cerebral emboli and stroke in this setting reside in the heart, heart valves, thoracic aorta, and great vessels when these structures are intervened thereon. Even simple cardiac catheterization with an endovascular catheter can induce microtrauma of the atherosclerotic thoracic aorta leading to formation of embolic particles with subsequent embolic brain injury ranging from latent ischemic foci to a massive or even fatal stroke.

Multiple devices are known that attempt to prevent embolization of the carotid arteries during endovascular and cardiac interventions. These anti-embolic devices, however, have not received wide acceptance in surgery of the heart, heart valves and thoracic aorta due to their complexity and invasive character with the risk of additional trauma to the inner vessel wall resulting in a high risk to benefit ratio. Known devices require insertion of additional hardware into the arterial system or aorta, a procedure that is known by itself to be associated with all classical risks of endovascular intervention, including aortic dissection, bleeding, thrombosis, and carotid cerebral embolization and stroke. One known intra-aortic filter device that is inserted into the ascending portion of the thoracic aorta via an aortic cannula to capture potential embolic material released from the heart and aortic wall during heart surgery was found to be quite difficult to implement and was reported to be associated with major trauma to aortic wall and acute aortic dissection.

Another such device for preventing emboli into the cerebral circulation Includes a porous deflector/trite-aortic shield that captures or diverts potential emboli into the distal vasculature. A yet additional device has also been proposed for use during aortic valve surgery and is an intra-aortic filter catheter that captures emboli during this procedure. It has been established that intravascular filters are not able to capture emboli smaller than the pore size of the available devices (currently 60-140 μm) resulting in cerebral microembolization. Embolization may also occur due to poor apposition of the filter to the aortic or carotid arterial wall.

Furthermore, the placement of the filter by itself may produce cerebral emboli. For example, the mere passing of a guide wire into a carotid artery generates approximately 40,000 microemboli, with a significant percentage of small, less than 60 μm, particles that are not retained by standard filters. Therefore, in spite of multiple innovations in the field of anti-embolic devices, the problem of cerebral emboli and stroke during cardiovascular surgery is far from being resolved.

It is known to use balloon occlusion catheters for the prevention of embolic stroke. In this regard, the balloon occlusion catheter is placed inside of one of the carotid arteries when a procedure, for example carotid angioplasty and stenting, is conducted on the carotid artery in question. Although capable of preventing stroke when a single carotid artery is operated upon, this device cannot work to prevent stroke during procedures on the heart and aorta, endovascular or open, and cannot provide for bilateral occlusion. This device cannot simultaneously occlude both the left and right carotid arteries to prevent flow simultaneously through both of these arteries, and thus cannot prevent stroke should emboli flow into the non-blocked carotid artery.

Also, the design of known endovascular devices did not address the issue of specific orientation of balloons in carotid arteries. By failing to address this issue, the methods cause an increase in the amount of time and effort needed to make the placement and likewise cause a safety concern.

Further, known endovascular carotid occluding devices require a guide wire to be inserted into the carotid arterial system. This procedure by itself is known to induce carotid trauma and cause the formation of cerebral emboli and resultant stroke. Still additionally, prior endovascular carotid occluding devices are not capable of reducing arterial flow through both right and left vertebral arteries, either at the same time or individually. This deficiency may allow emboli to enter vertebral circulation and cause stroke.

Still further, known systems are not capable of interrupting the flow, if needed, to both vertebral arteries for the period of time when emboli can enter cerebral circulation. Known systems also risk trauma to the carotid artery wall and allow for subsequent cerebral emboli. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended Figs. in which:

FIG. 12 is a perspective view of an, apparatus that includes an insertion device and two occluding catheters.

FIG. 13 is a cross-sectional view taken along line 13-13 of FIG. 12.

FIG. 14 is a perspective view of an insertion device.

Figure 1:
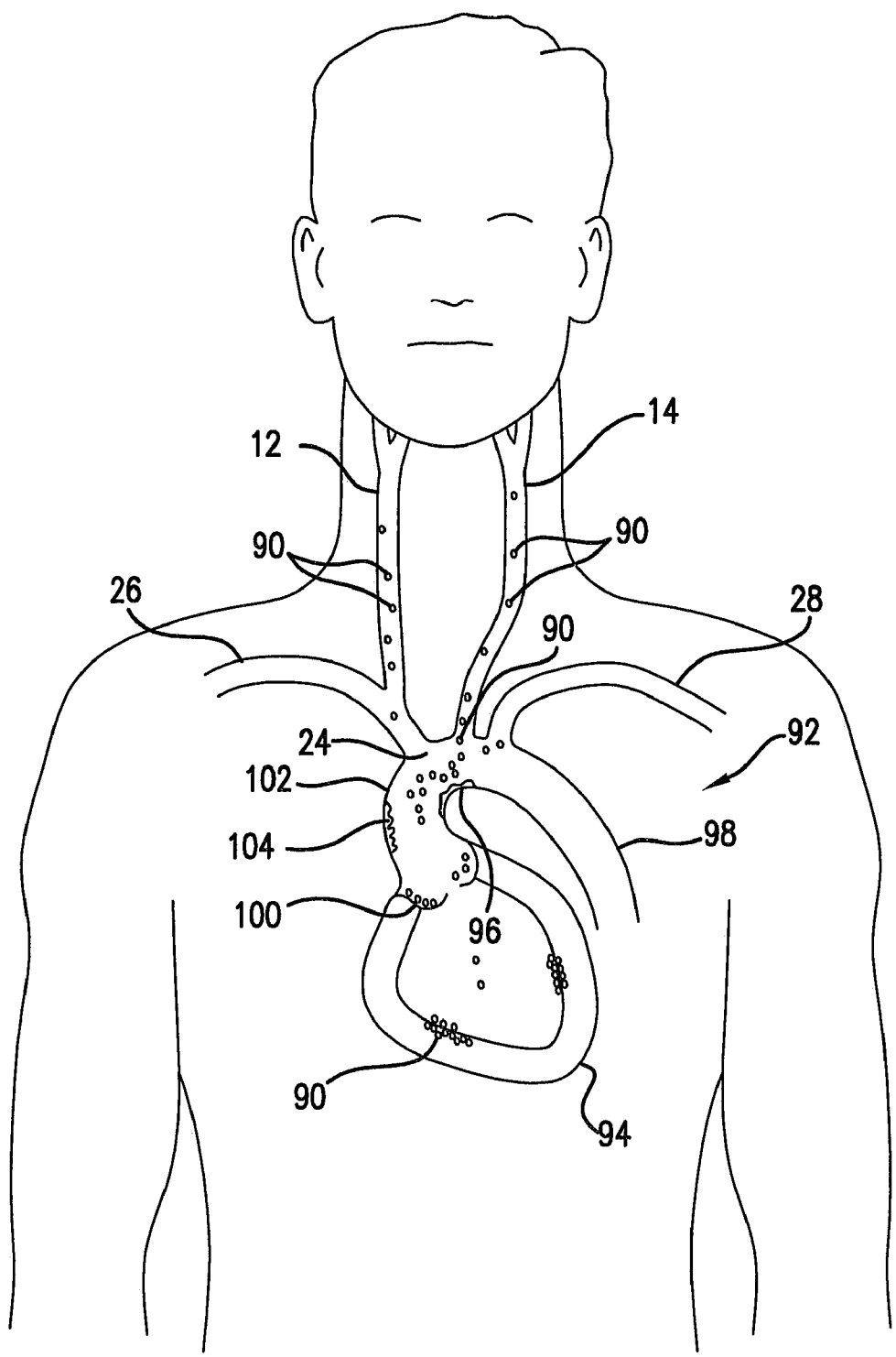
FIG. 1 is a front view of a patient with emboli in the heart and ascending thoracic aorta with subsequent propagation of emboli into both carotid arteries with the source of emboli being diseased aorta, aortic valve and the heart.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

The present invention provides for an apparatus 10 that has a first occluding catheter 16 that carries a first occluding balloon 18, and a second occluding catheter 20 that carries a second occluding balloon 22. The occluding catheters 16 and 20 can be introduced into the circulatory system 92 of a patient and the occluding balloons 18, 22 can be inflated in order to occlude blood flow through the right carotid artery 12 and the left carotid artery 14 at the same time. This may occur during a surgical procedure that releases emboli 90 that would otherwise flow through the carotid arteries 12, 14 and cause stroke or other damage to the patient. Blockage of both carotid arteries 12, 14 causes the emboli 90 to be routed primarily or fully down through the descending aorta 98. The apparatus 10 may include an insertion device 58 that can first be placed into the circulatory system 92 so that the occluding catheters 16, 20 can be subsequently inserted and more easily positioned within the circulatory system 92.

With reference to FIG. 1, a front view of a patient is shown in which emboli 90 are transferred from the aortic arch 96 into the carotid arteries 12, 14. The emboli 90 that are present in the carotid arteries 12, 14 can then be transferred into the cerebral circulation causing stroke of the patient. The emboli 90 may be fragments of atherosclerotic plaque 104 of the ascending aorta 96 that become dislodged during manipulation of the ascending thoracic aorta 102. Also shown in FIG. 1 is calcification of the aortic valve 100 and intracardiac emboli 90 of the heart 94 that can also be the origin of emboli 90 eventually present in the carotid arteries 12, 14. The intracardiac emboli 90 may include air, gas, thrombi and atherosclerotic materials. Although all of the various emboli 90 in the heart 94, aortic arch 96, ascending aorta 102, and aortic valve 100 need not be present in all instances they are all shown in FIG. 1 for sake of example.

Trauma to the heart 94, aortic valve 100 and aortic structures during placement and removal of items such as aortic clamps and electrophysiological instruments, along with manipulations such as coronary artery bypass grafting, aortic and mitral valve replacement, catheter ablation, endovascular grafting of the aorta 96, balloon valvuloplasty percutaneous implantation of the aortic or mitral valves, endovascular manipulations on the aorta 96, aortic branches and the heart 94 may give rise to the presence of emboli 90 in the carotid arteries 12, 14. Critical moments of the aforementioned procedures (for example during the aortic cross clamp manipulation, percutaneous aortic and mitral valvuloplasty or valve implantation, coronary interventions, endovascular grafting of the aorta 96 and its branches, and endovascular procedures on the aorta 96) may cause emboli 90 to form and cause stroke and are referred to as "embolic" events.

Figure 2:
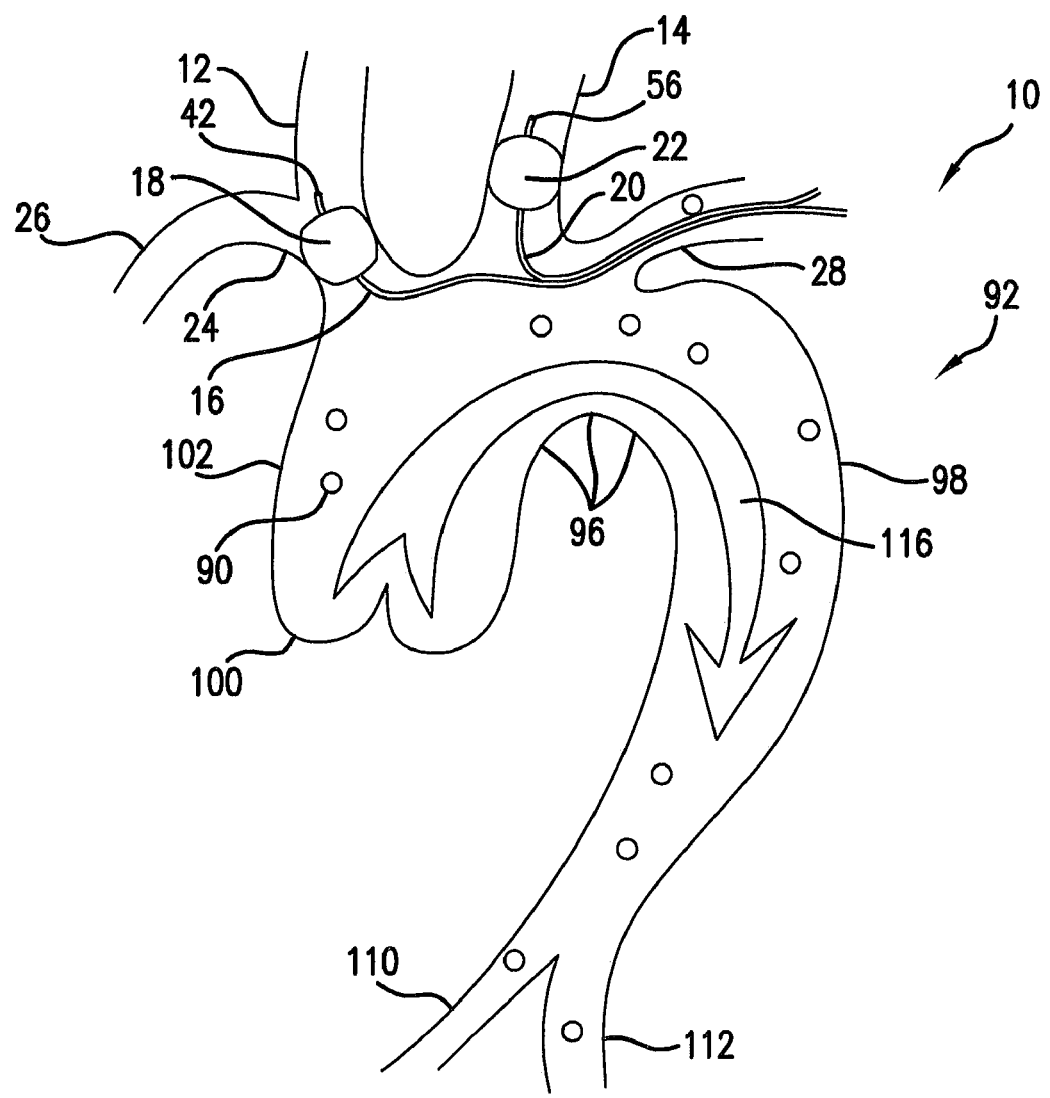
FIG. 2 is a front view of the circulatory system with a first occluding balloon in an innominate artery and a second occluding balloon in a left carotid artery.
Figure 3:
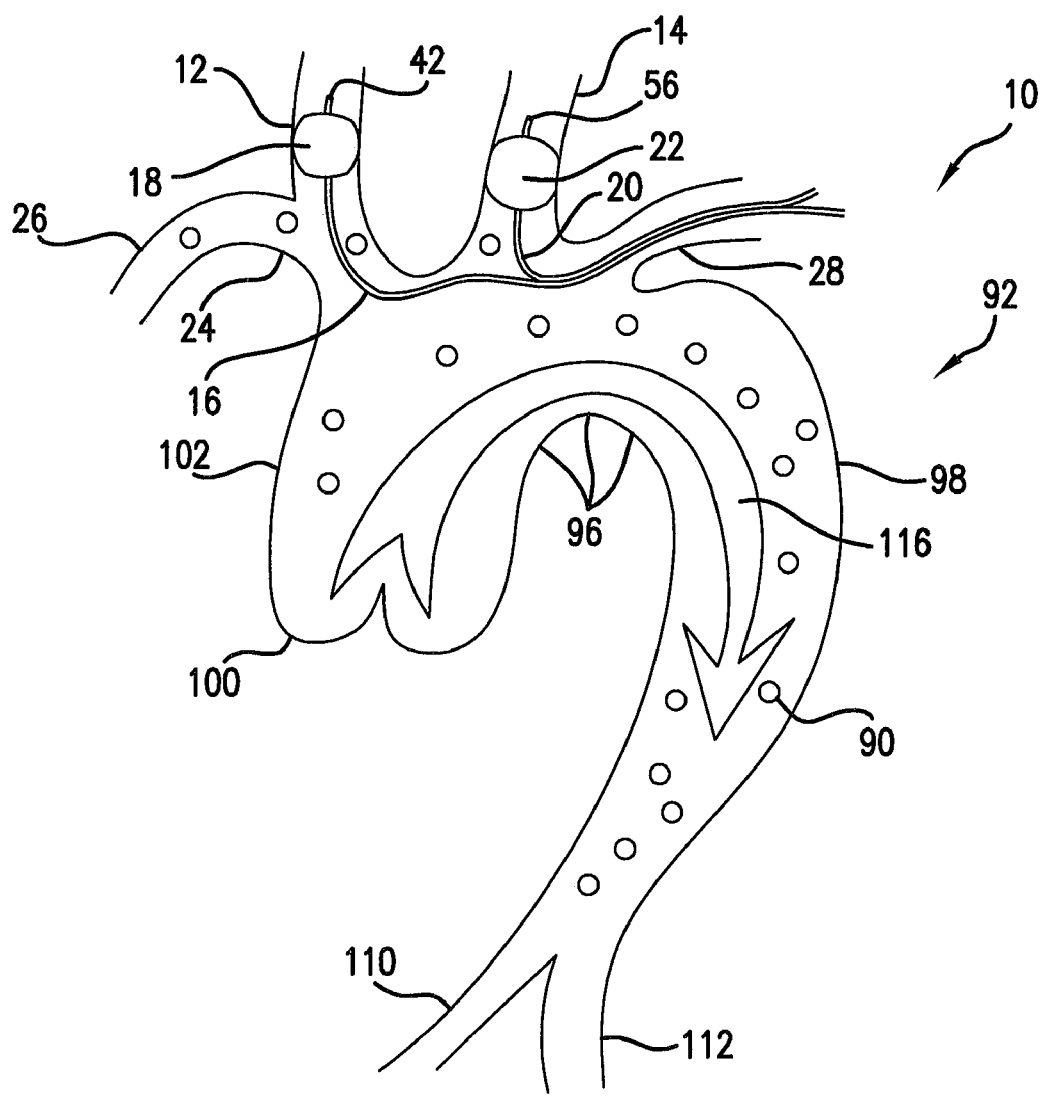
FIG. 3 is a front view of the circulatory system with a first occluding balloon in a right carotid artery and a second occluding balloon in a left carotid artery.

FIGS. 2 and 3 disclose exemplary embodiments of the invention in which the first and second occluding balloons 18 and 22 are simultaneously inflated. The second occluding balloon 22 is shown in the inflated position within the left carotid artery 14 and occludes the left carotid artery 14. The first occluding balloon 18 is shown positioned within the innominate artery 24 in FIG. 2 and occludes both the right carotid artery 12 and the right subclavian artery 26. However, in FIG. 3 the first occluding balloon 18 is in the inflated configuration and is located in the right carotid artery 12 occluding the right carotid artery 12 but not occluding the right subclavian artery 26. In both configurations, all potential emboli 90, released due to manipulations on atherosclerotic calcified plaques 104 of the ascending aorta 102 or from other sources as previously discussed, will be diverged downstream from the cerebral circulation into the descending aorta 98, thus protecting the patient from embolic stroke.

The temporary interruption of flow at the level of the proximal carotid arteries 12, 14 leads to the divergence of blood flow, as indicated by arrow 116, and carries all potential cerebral emboli 90 into the distal aorta 98 and femoral arteries 110, 112. With reference to FIG. 2, the position of the first occluding balloon 18 can be adjusted by placing it right at the bifurcation of the innominate artery 24 in order to completely interrupt the arterial inflow to the right carotid artery 12 and the right subclavian artery 26. This placement may protect not only the right carotid artery 12, but also the right vertebral circulation from emboli by virtue of blocking the arterial inflow to these vessels through the right subclavian artery 26. In both FIGS. 2 and 3, the first and second occluding catheters 16, 20 are introduced through the left subclavian artery 28. The size of the catheters 16, 20 may be such that they fill the left subclavian artery 28 and block blood flow through the left subclavian artery 28 thus preventing emboli 90 from entering the left vertebral circulation. However, in other embodiments, emboli 90 may be allowed to enter the left vertebral circulation through the left subclavian artery 28 as the left subclavian artery 28 may not be fully blocked by the catheters 16, 20.

Figure 4:
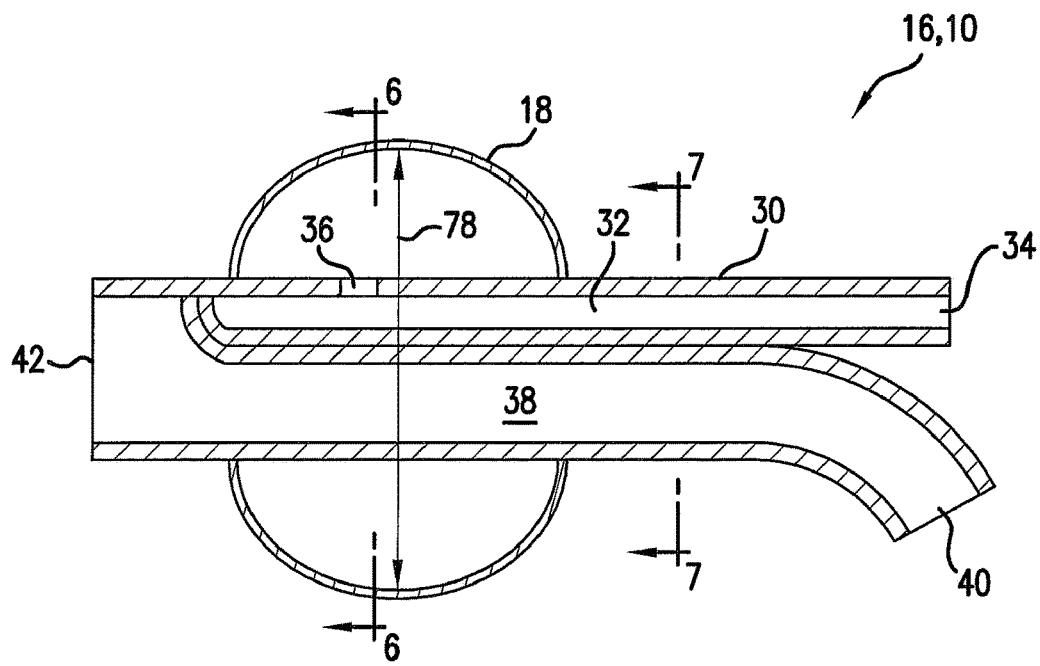
FIG. 4 is a front cross-sectional view of a first occluding catheter.
Figure 6:
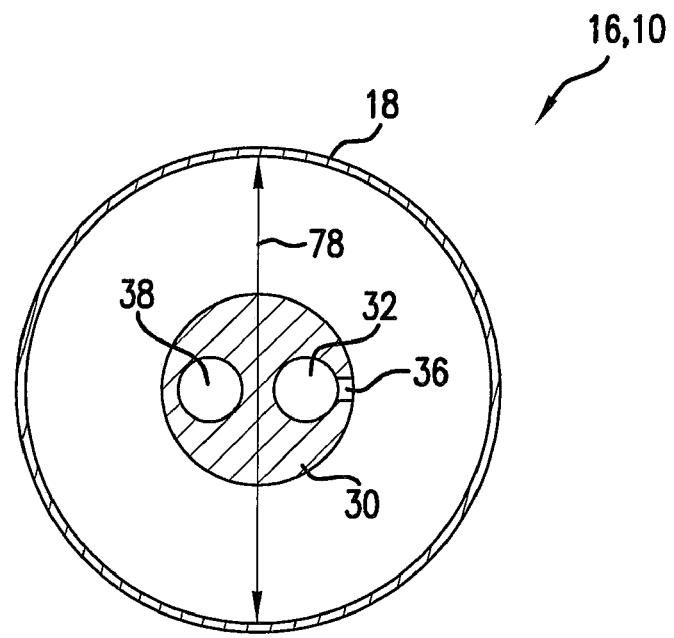
FIG. 6 is a cross-sectional view taken along line 6-6 of FIG. 4 with the additional cross-sectional half added.
Figure 7:
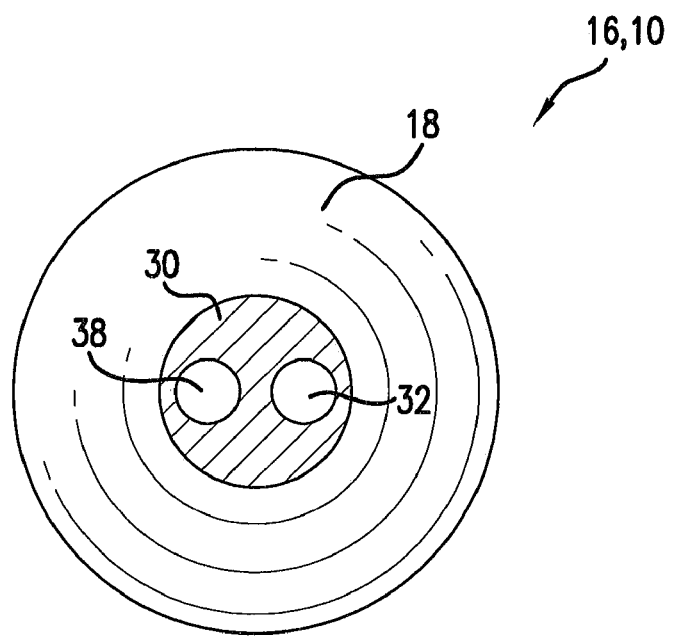
FIG. 7 is a cross-sectional view taken along line 7-7 of FIG. 4 with the additional cross-sectional half added.

The first occluding catheter 16 is shown in greater detail with reference to FIGS. 4, 6 and 7. The first occluding balloon 18 is shown in the inflated configuration. The first occluding catheter 16 has a first occluding catheter shaft 30 that may be of any length, diameter, shape, or size. The first occluding catheter shaft 30 can define a first inflation channel that extends from a first proximal inflation port 34 at a proximal end of the shaft 30 to a location close to or at the first occluding balloon 18. A first occluding balloon opening 36 is defined by the first occluding catheter shaft 30 and places the first inflation channel 32 into fluid communication with the interior of the first occluding balloon 18. A fluid pressure sources such as a syringe or pump can be connected to the first proximal inflation port 34 and actuated in order to force air, gas, liquid, or any other type of fluid through the first inflation channel 32 and into the first occluding balloon 18 to place the first occluding balloon 18 into the inflated configuration shown in FIG. 4. Once one desires to deflate the first occluding balloon 18, the pressure may be released or the fluid may otherwise be withdrawn from the first occluding balloon 18 back in the proximal direction through the first inflation channel 32. The first occluding balloon 18 may have any size or shape and can be made of a material resilient yet strong enough to allow for repeated inflation and deflation.

The first occluding catheter shaft 30 may also define a first pressure measurement channel 38 that can extend completely through the shaft 30 from its proximal end to its distal end. The first pressure measurement channel 38 may extend from a first proximal measurement port 40 on the proximal end to a first distal opening 42 at the extreme distal tip of the first occluding catheter shat 30. The first pressure measurement channel 38 may be used to measure pressure of the circulatory system 92 at a location distal to the inflated first occluding balloon 18 and thus the pressure of the circulatory system 92 at the first distal opening 42 or just distally past the first distal opening 42. In this regard, a pressure measurement device, for example a manometer 106 can be placed into fluid communication with the first pressure measurement channel 38 by connection at the first proximal measurement port 40 and have access to the pressure of the circulatory system 92 at a location at or distal to the first distal opening 42.

The channels 32 and 38 are shown as being circular in cross-sectional shape, but it is to be understood that they may be variously shaped in accordance with other exemplary embodiments. Also, although shown as having but a single first occluding balloon opening 36, any number of openings 36 may be present in other arrangements. Still further, although shown as having but a single first occluding balloon 18, any number of balloons 18 can exist in other arrangements. For example, from 2-5, from 6-10, or up to 20 occluding balloons 18 may be present on the first occluding catheter 16 in other exemplary embodiments.

Figure 5:
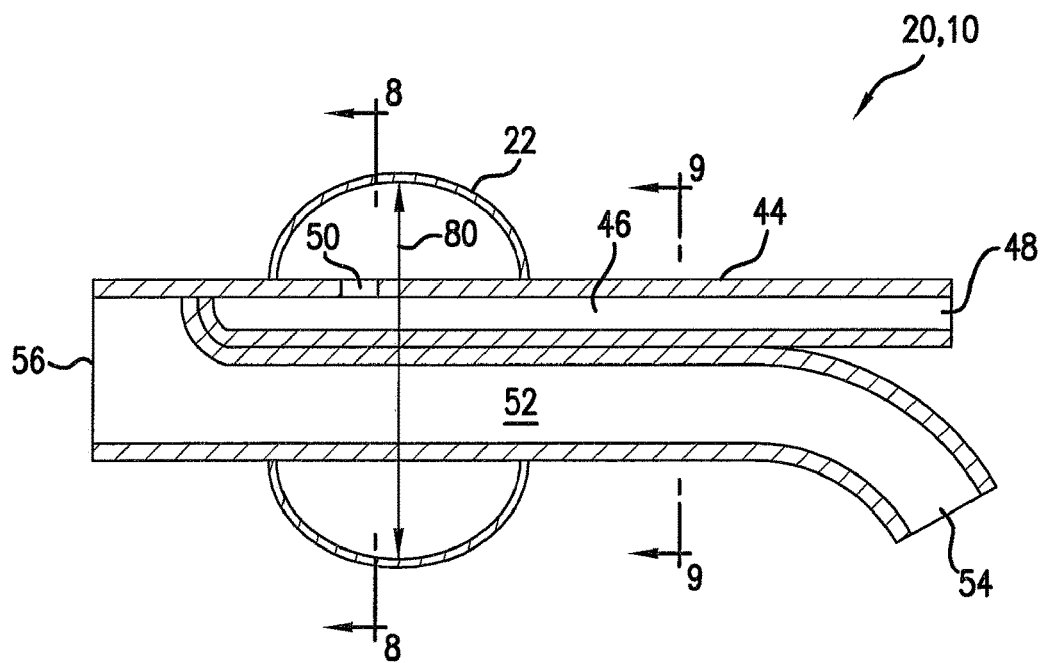
FIG. 5 is a front cross-sectional view of a second occluding catheter.
Figure 8:
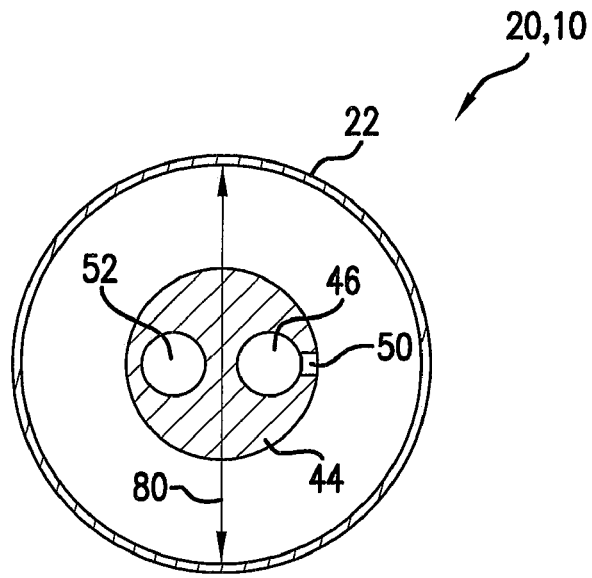
FIG. 8 is a cross-sectional view taken along line 8-8 of FIG. 5 with the additional cross-sectional half added.
Figure 9:
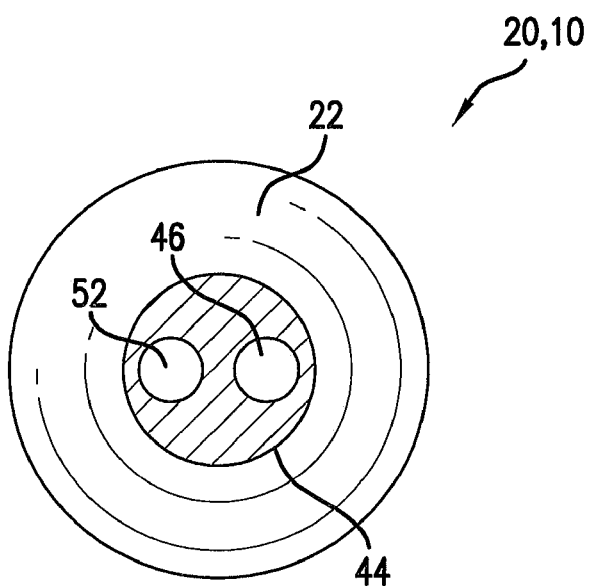
FIG. 9 is a cross-sectional view taken along line 9-9 of FIG. 5 with the additional cross-sectional half added.

A more detailed view of the second occluding catheter 20 is shown in FIGS. 5, 8 and 9. The second occluding catheter 20 includes a second occluding catheter shaft 44 that defines a second inflation channel 46 that extends from a second proximal inflation port 48 to a second occluding balloon opening 50. The second occluding catheter shaft 44 also defines a second pressure measurement channel 52 that extends from a second proximal measurement port 54 to a second distal opening 56. The various components of the second occluding catheter 20 can be arranged in the same manners are those previously discussed above with respect to the first occluding catheter 16 and a repeat of this information is not necessary.

The first and second occluding catheters 16 and 20 may be arranged in the same manner as one another but may be sized differently from one another such that the shafts 30, 44 are different lengths from one another. The diameter, volume and length of the occluding balloons 18, 22 may also vary according to patient's anatomy with the occluding balloon 18, 22 that is to be disposed within the innominate artery 24 being 50-100% longer and larger than the occluding balloon 18, 22 for the occlusion of the left carotid artery 14. In this regard, the first diameter 78 may be 50-100% larger than the second diameter 80. However, in other embodiments, the first diameter 78 may be the same size as the second diameter 80, may be 10-25% larger, 10-25% smaller, 25-50% larger, 25-50% smaller, 50-200% larger, 50-200% smaller, 200-500% larger or 200-500% smaller in accordance with various exemplary embodiments.

Figure 10:
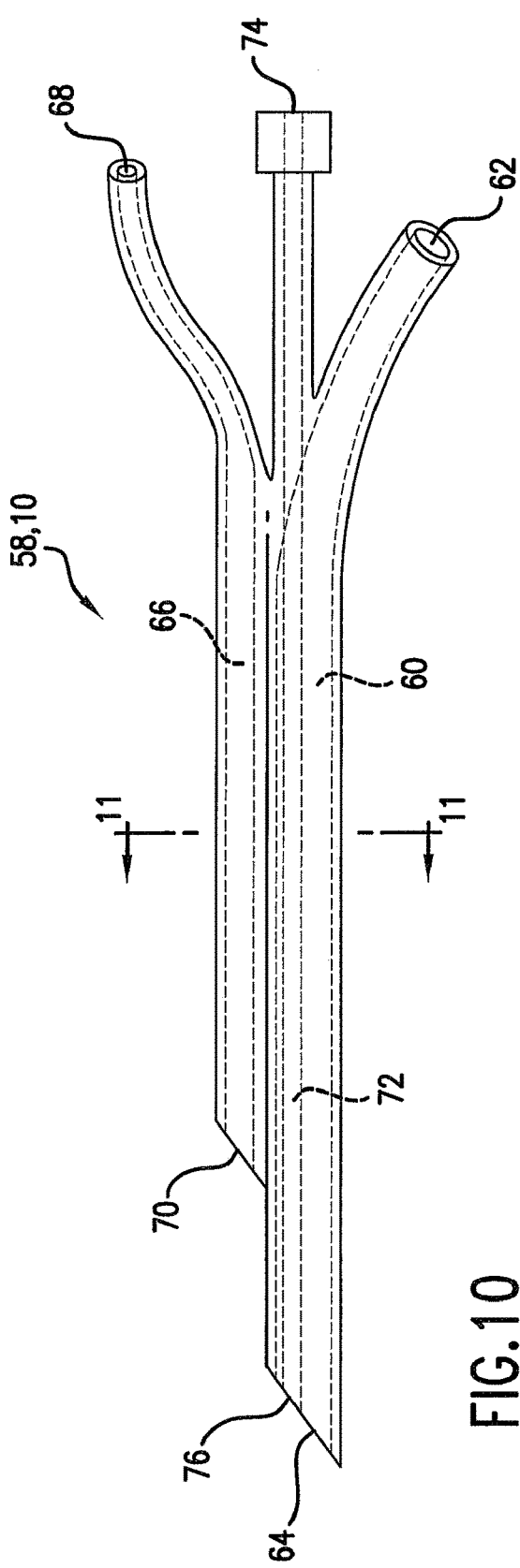
FIG. 10 is a side view of an insertion device.
Figure 11:
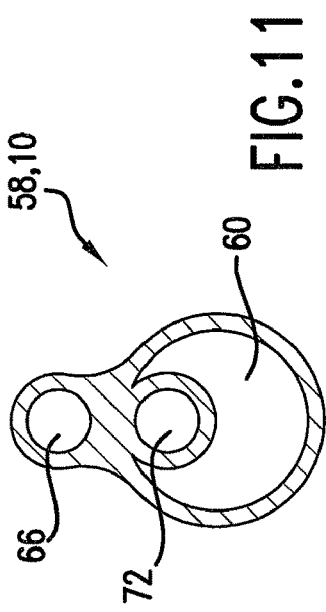
FIG. 11 is a cross-sectional view taken along line 11-11 of FIG. 10.

The apparatus 10 may also include an insertion device 58 in certain exemplary embodiments that can function to help properly position the first, and second occluding catheters 16, 20 within the circulatory system 92. FIGS. 10 and 11 illustrate one exemplary embodiment of the insertion device 58 that has a shaft that defines three channels 60, 66 and 72 that are through channels that extend through the insertion device 58. The shaft of the insertion device 58 may define a first occluding catheter channel 60 that extends from an insertion device first proximal opening 62 at the proximal end of the insertion device 58 to an insertion device first distal opening 64 at the distal end of the insertion device 58. The insertion device first distal opening 64 is located at a tapered distal edge of the insertion device 58 and has a cross-sectional shape that is generally oval that has both convex and concave surfaces.

The insertion device 58 also includes a second occluding catheter channel 66 that is also a through channel of the shaft of the insertion device 58 that to extends from an insertion device second proximal opening 68 at the proximal end of the insertion device 58 to an insertion device second distal opening 70. The second occluding catheter channel 66 has a cross-sectional shape in the form of an oval. The second occluding catheter channel 66 is shorter in length than the first occluding catheter channel 60 and is located off center from the first occluding catheter channel 60 so that the channels 60 and 66 are not coaxial with one another. The insertion device second distal opening 70 is located at a surface of the insertion device 58 that is angled or tapered such that it is not a flat surface.

The shaft of the insertion device 58 also defines a pressure measurement channel 72 that is a through channel of the insertion device 58 and extends from a pressure measurement proximal opening 74 at the proximal end of the insertion device 58 to a pressure measurement distal opening 76. The pressure measurement channel 72 has a circular cross-sectional shape and is offset from and not coaxial with either the first occluding catheter channel 60 or the second occluding catheter channel 66. The pressure measurement channel 72 can be used for irrigation and pressure measurement distal to the pressure measurement distal opening 76.

The openings 64 and 70 can be positioned so that they face in a direction that is angled to a direction along the longitudinal axis of the shaft of the insertion device 58. The axis of the openings 64 and 70 are not coaxial with the axis of the shaft of the insertion device, and extend in the same direction as one another such that the openings 64 and 70 open onto a common side of the shaft of the insertion device 58. This arrangement may assist the first and second occluding catheters 16, 20 in being properly positioned in the circulatory system 92.

The first and second occluding catheters 16, 20 may be inserted through the insertion device 58 such that the insertion device 58 is used to position the catheters 16, 20 within the circulatory system 92. With reference to FIGS. 12-14, the first occluding catheter 16 can be introduced through the insertion device first proximal opening 62 and into the first occluding catheter channel 60. The first occluding catheter 16 may be moved relative to the insertion device 58 such that the first occluding balloon 18, that can be uninflated, is moved out of the insertion device first distal opening 64 and out of the channel 60. In a similar manner, the second occluding catheter 20 can be moved through the insertion device second proximal opening 68 and into the second occluding catheter channel 66. The second occluding balloon 22 may be moved out of the insertion device second distal opening 70 and thus out of the channel 66. The catheters 16, 20 may be located within the insertion device 58 when the apparatus 10 is used to occlude the right and left carotid arteries 12, 14.

A first syringe 82 can be connected to the first proximal inflation port 34, and a second syringe 84 can be connected to the second proximal inflation port 48. Actuation of the syringes 82, 84 may function to inflate the first and second occluding balloons 18, 22 as previously discussed. In other arrangements, a single syringe can be placed into fluid communication with the ports 34 and 48 and used to inflate both of the balloons 18, 22. The first proximal measurement port 40 can be connected to a manometer 106 so that the pressure at the first distal opening 42 can be measured. Similarly, the second proximal measurement port 54 can be connected to the same or different manometer 106 so that the pressure at the second distal opening 56 can be measured. Although not shown in FIG. 12, the pressure measurement proximal opening 74 can be connected to a manometer 106 so that the pressure at the pressure measurement distal opening can be measured.

The space between the insertion device first distal opening 64 and the insertion device second distal opening 70 in the longitudinal/axial direction of the shaft of the insertion device 58 can be selected to correspond to the distance between the innominate artery 24 and the left carotid artery 14 orifice on the inner surface of the aortic arch 96. The distance between the openings 64 and 70 may be selected to roughly correspond to the orifices within the circulatory system 92 that one desires catheters 16, 20 to be inserted upon exiting the openings 64 and 70. The desired spacing of the openings 64 and 70 may be achieved by selecting or creating an introducer device 58 that has dimensions that match the distance between the orifices of the left carotid artery 14 and the innominate artery 24 at the aortic arch 96 as estimated by preoperative CT scan. In some instances, the distance between openings 64 and 70 in the longitudinal/axial direction of the shaft of the insertion device 58 may be between 0.5 centimeters and 5.5 centimeters. Use of properly spaced openings 64 and 70 may achieve safer and easier advancement of the first and second occluding catheters 16, 20 without trauma to the carotid arteries 12, 14 or the aortic arch 96.

Figure 15:
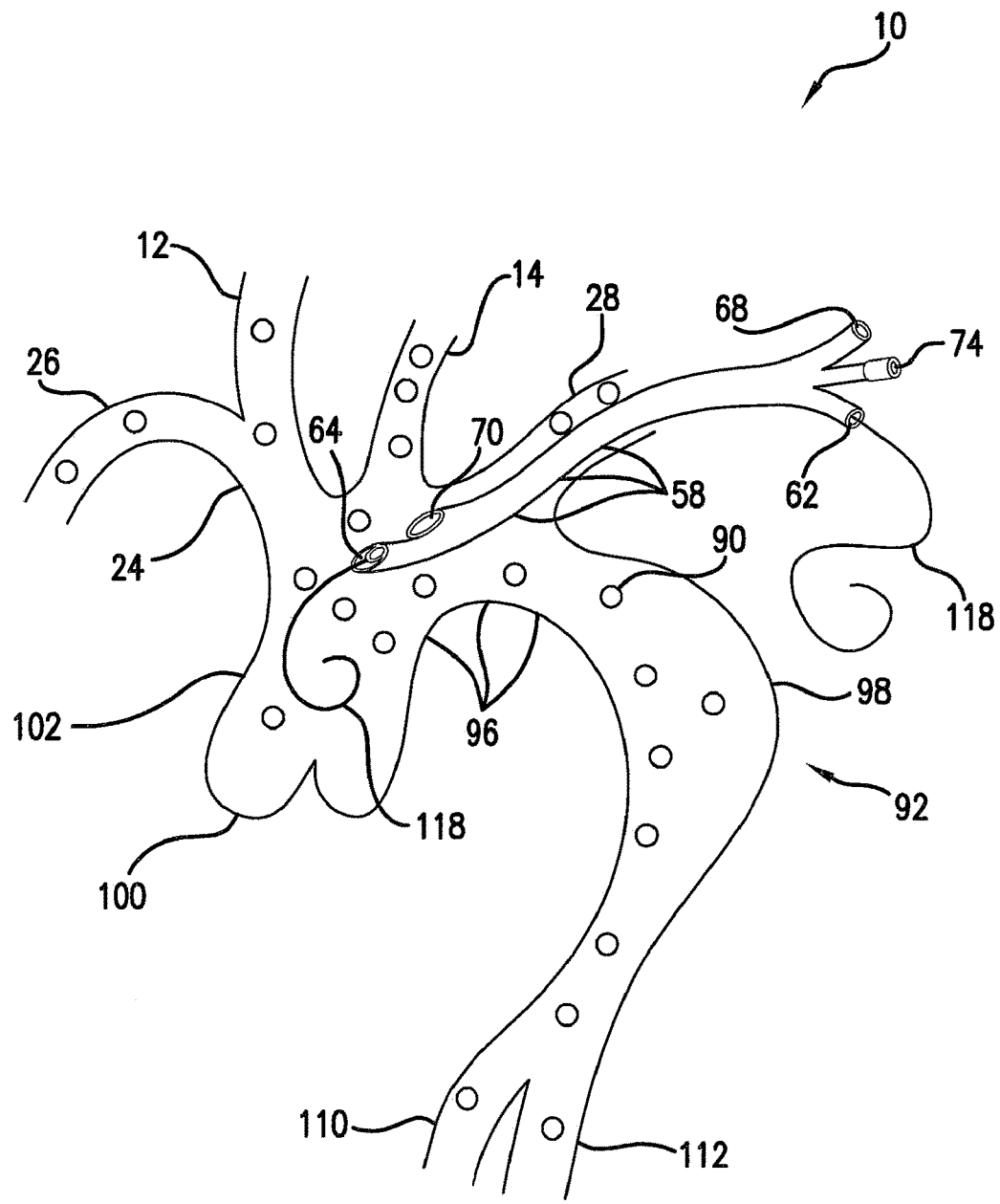
FIG. 15 is a front view of the circulatory system that shows placement of an insertion device with the aid of a guide wire.

With reference to FIG. 15, the insertion device 15 may be inserted via a left arm approach and advanced into the left subclavian artery 28 and into the aortic arch 96 using fluoroscopic control. A flexible guide wire 118 may be used for this part of the procedure. However, the use of a guide wire 118 is not needed in other exemplary embodiments, and the insertion device 58 if used may be placed without the aid of a guide wire 118. Further, the use of an insertion device 58 is not needed in other exemplary embodiments. The occluding catheters 16, 20 may be naturally propelled into the target vessel with forward arterial flow thus following the natural direction of the blood stream into the innominate artery 24 and both carotid arteries 12, 14. This feature may be achieved by using highly compliant and flexible material for the construction of the shafts of the catheters 30 and 44 and by inflating the occluding balloons 18 and 22 after their insertion.

The portions of the insertion device 58 forming the insertion device first distal opening 64 and the insertion device second distal opening 70 may be radiopaque and can be positioned to face the orifices of the left carotid artery 14 and the innominate artery 24 on the aortic arch 96. Next, the guide wire 118 if used may be removed. Alternatively, the guide wire 118 if used may be left in place. The guide wire 118 if used may be placed through any of the channels 60, 66 and 72. Still further, in some embodiments the guide wire 118 may be inserted through the first pressure measurement channel 38 and the second pressure measurement channel 52. The guide wire 118 is not inserted and is not located within the first inflation channel 32 or the second inflation channel 46.

Figure 16:
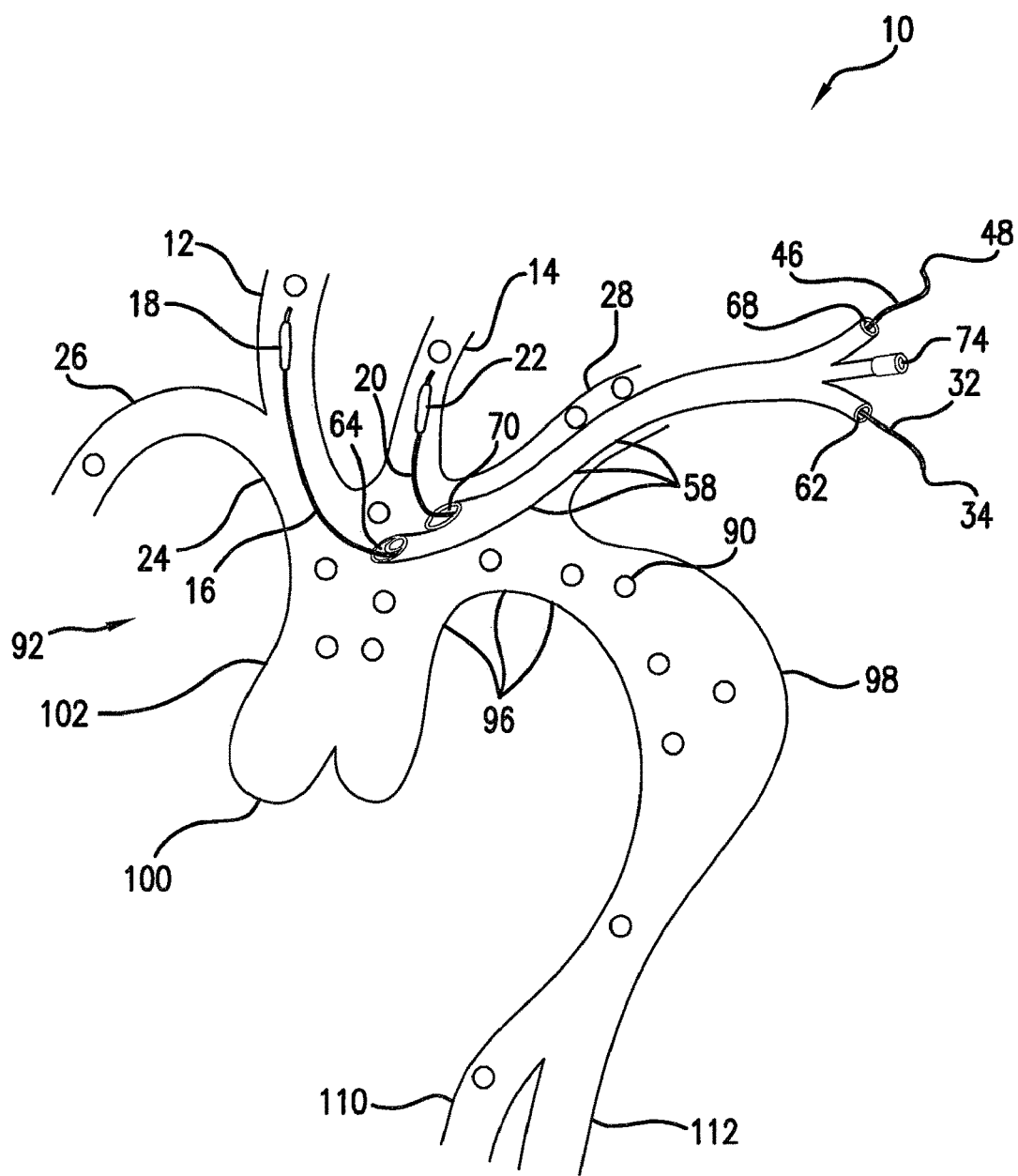
FIG. 16 is a front view of the circulatory system with two occluding catheters with uninflated occluding balloons introduced through the insertion device.

With reference now to FIG. 16, the first occluding catheter 16 may be advanced through the insertion device first proximal opening 62 and through the insertion device first distal opening such that the deflated first occluding balloon 18 exits the insertion device first distal opening. The second occluding catheter 20 may be advanced through the insertion device second proximal opening 68 and the second occluding catheter channel 66 such that the deflated second occluding balloon 22 exits the insertion device second distal opening 70. Once the first and second occluding balloons 18 and 22 are out of the insertion device 58 they may be advanced into the vessels that are desired to be occluded. In the exemplary embodiment shown, the first occluding balloon 18 is advanced into the right carotid artery 12 and the second occluding balloon 22 is advanced into the left carotid artery 14. The process of advancement may be facilitated by partial or complete inflation of the first and second occluding balloons 18, 22 while the first and second occluding catheters 16, 20 remain in the aortic arch 96 to achieve the effect of propulsion of the balloons 18, 22 into the target blood vessels with arterial blood flow. The inflated first occluding balloon 18 may be naturally propelled by arterial blood flow into the innominate artery 24 and if desired the right carotid artery 12, and the inflated second occluding balloon 22 may be carried by arterial blood flow into the left carotid artery 14. In other arrangements, the occluding balloons 18, 22 are not inflated prior to positioning and are only inflated or even only partially inflated once they are positioned within their appropriate arteries 12, 14.

The adequacy of the position of the occluding balloons 18, 22 can be confirmed by fluoroscopy, angiography, and by dampened arterial pressure recorded at the first distal opening 42 and the second distal opening 56 that are located downstream from the areas of occlusion. The ideal position of the first occluding balloon 18 may be at the proximal segment of the right carotid artery 12 or the distal segment of the innominate artery 24, and the best position of the second occluding balloon 22 may correspond to the proximal segment of the left carotid artery 14. Once the occluding balloons 18, 22 are properly positioned they may be deflated and then considered ready for use. The insertion device 58 if used may be present during use of the occluding balloons 18, 22 or may be removed before use of the occluding balloons 18, 22.

Figure 17:
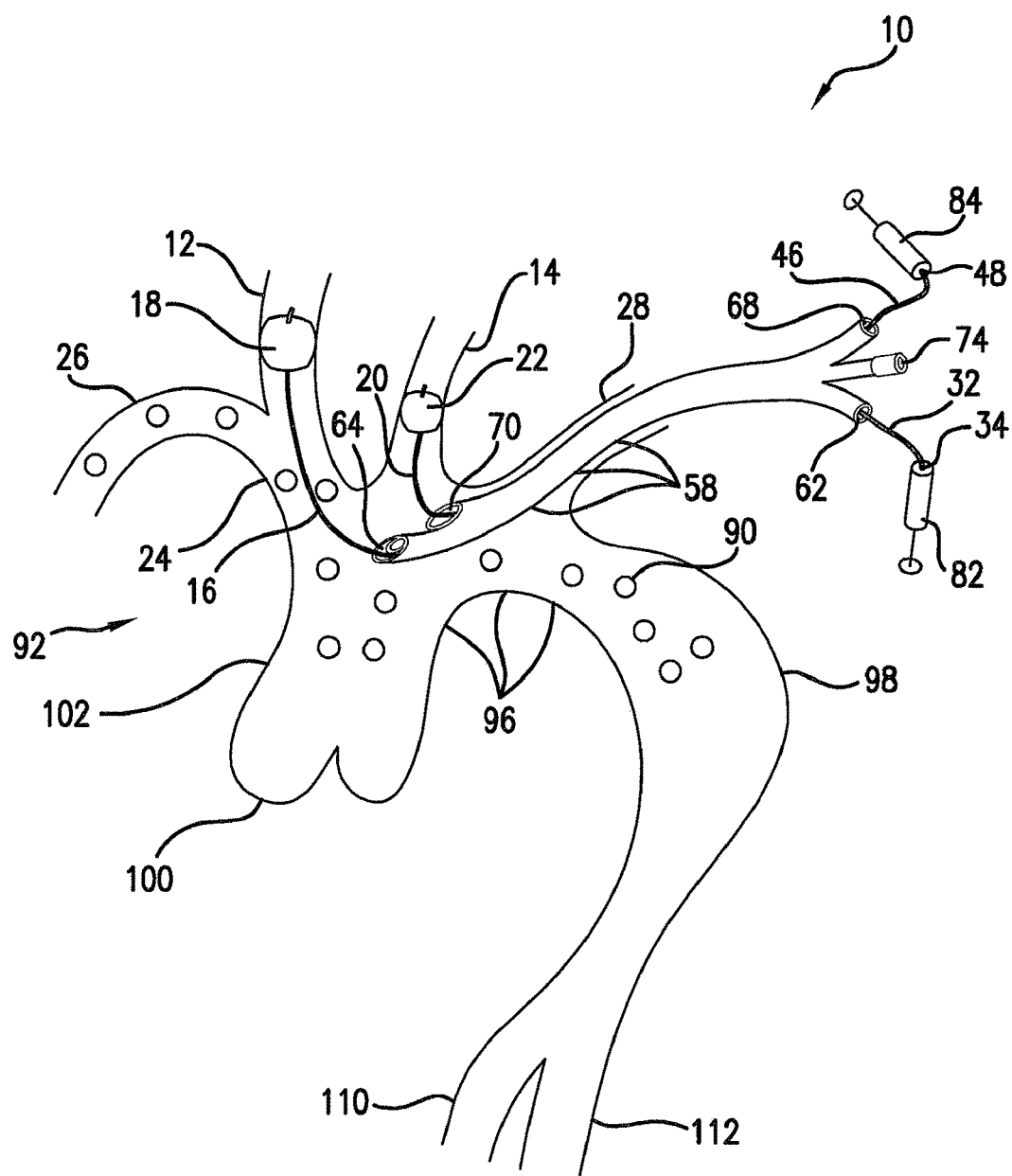
FIG. 17 is a front view of the circulatory system with two inflated occluding balloons positioned in the right and left carotid arteries.

FIG. 17 shows the apparatus 10 positioned within the circulatory system 92 and used to deflect emboli 90. Right before proceeding with emboligenic part of surgery or endovascular intervention the first and second occluding balloons 18, 22 are inflated using syringes 82, 84 attached to the first proximal inflation portion 34 and the second proximal inflation port 48 to provide temporary obstruction of arterial blood flow through the right carotid artery 12 and left carotid 32 artery. As a result all potential emboli 90, formed secondary to the main intervention on the heart 94, coronary arteries and aorta 96 will be diverted into the distal aorta 98, and peripheral arteries 110, 112. If the right subclavian artery 26 is not blocked, emboli 90 may flow through this artery 26. The presence of the insertion device 58 in the left subclavian artery 28 may function to block emboli 90 from flowing through the left subclavian artery 28, however some emboli 90 may in fact flow through the left subclavian artery 28.

Figure 18:
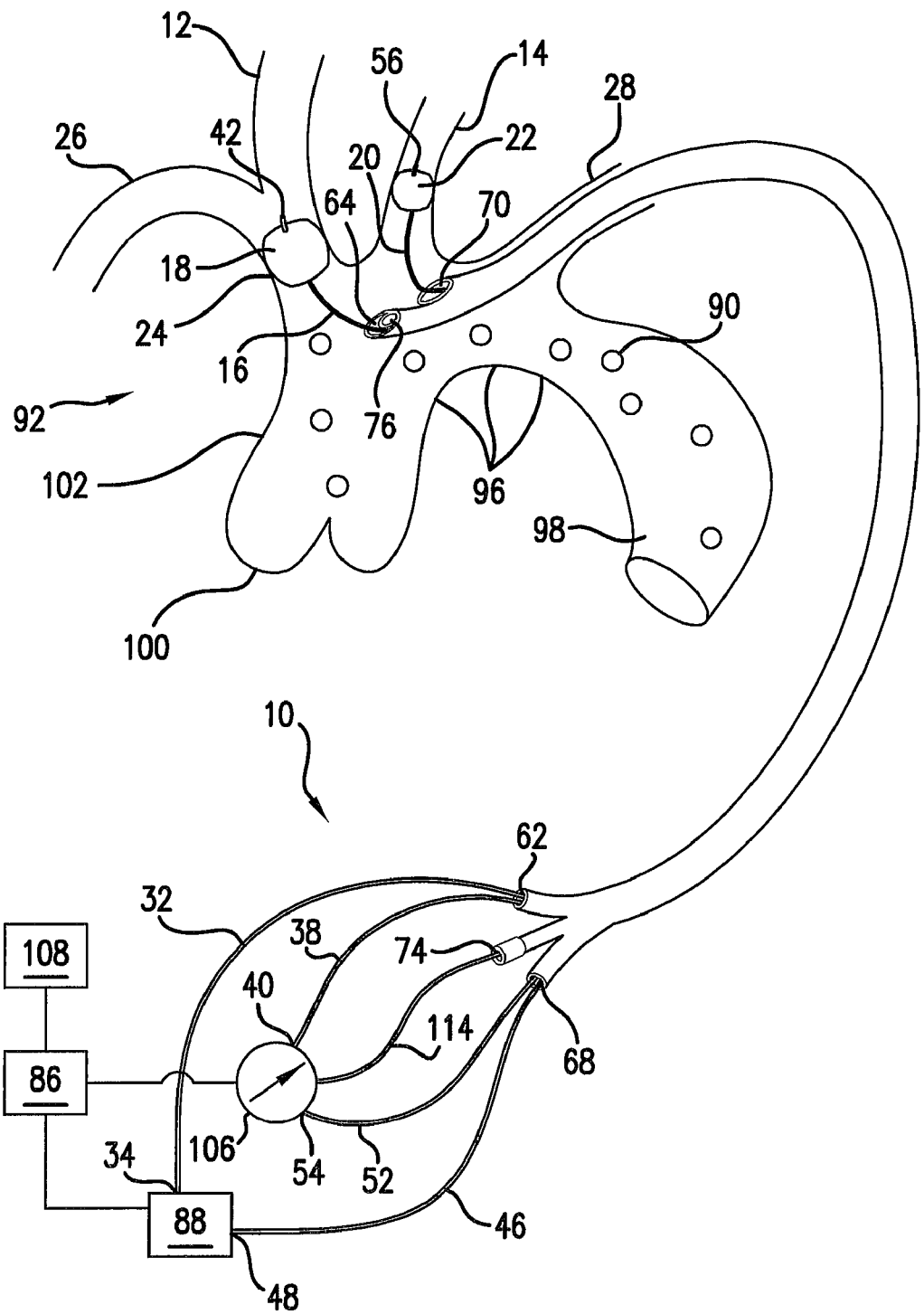
FIG. 18 is a front view of the circulatory system with two inflated occluding balloons, positioned in the innominate and left carotid arteries, with the alarm system and pressure supply.

FIG. 18 shows placement of the first occluding balloon 18 within the innominate artery 24 and the second occluding balloon 22 in the left carotid artery 14. Occlusion of these arteries 24 and 14 will cause emboli 90 to be diverted into the descending aorta 98 and away from and not into the right subclavian artery 26, right carotid artery 12, and left carotid artery 14. Emboli 90 may be capable of flowing through the left subclavian artery 28 or may be blocked due to the presence of the insertion device 58 in the left subclavian artery 28. Leaving the insertion device 58 within the left subclavian artery 28 during the time of inflation of the occluding balloons 18, 22 may cause the insertion device 58 to block emboli 90 from passing through the left subclavian artery 28.

The interruption of carotid flow or pulse may be assessed by angiography, carotid Doppler, or arterial pressure and waveform patterns distal to the level of occlusion in accordance with certain exemplary embodiments. In addition, percutaneous cerebral oximetery, electroencephalography and transcranial Doppler monitoring can be applied. In other arrangements, it may not be the case that this monitoring is applied in order to confirm positioning of the occluding balloons 18, 22.

Once the position of the occluding balloons 18, 22 is achieved the insertion device 58 may be pulled back into the lumen of the left subclavian artery 28. The insertion device 58 may be located in the left subclavian artery 28 during inflation and use of the apparatus 10. Alternatively, the insertion device 58 may be completely removed from the circulatory system 92 during use of the apparatus 10, or may remain within the aortic arch 96 during use of the apparatus 10.

Considering the fact that the length of most manipulations, associated with formation of cerebral emboli 90 rarely exceeds 1-2 minutes, a temporary interruption of the carotid flow for this period of time, plus 0.5-1.5 minutes to allow for complete washout of emboli 90 form the aorta 96 is completely safe and feasible. Thus, the time of interruption of flow through both carotid 12, 14 and vertebral arteries 26, 28 (if performed) should not exceed 1.5-3.5 minutes. This amount of time is usually sufficient to allow for complete washout of particulate matter and air from the heart 94, aortic valve 100, ascending aorta 102 and aortic arch 96 into descending aorta 98 and distal vasculature 110, 112 without inducing ischemic brain injury.

A manometer 106 may be in communication with the first distal opening 42, second distal opening 56, and pressure measurement distal opening 76. The first proximal measurement port 40 and the second proximal measurement port 54 can be connected to the manometer 106. A pressure measurement line 114 can be provided and be connected to the manometer 106 and to the pressure measurement proximal opening 74. A pressure supply 88 is in communication with the first proximal inflation port 34 and the second proximal inflation port 48 to provide inflation pressure for the first and second occluding balloons 18, 22. An alarm system 86 is in communication with the pressure supply 88 and manometer 106. Should the physician or physician's assistant forget to deflate the occluding balloons 18, 22 in a timely fashion, an alarm would go off and the occluding balloons 18, 22 would deflate spontaneously to avoid undue interruption of the cerebral flow. The alarm could be also triggered by the occurrence of emboli 90 detected by transcranial Doppler 108 (also in communication with the alarm system 86), echocardiography 108 (also in communication with the alarm system 86), or any other means, thus indicating an urgent need for temporary occlusion of the cerebral flow. Here, the alarm system 86 will cause inflation of the occluding balloons 18, 22. The alarm system 86 along with deflation or inflation of the occluding balloons 18, 22 could be overridden by the physician when clinically indicated.

After deflation of the occluding balloons 18, 22 the procedure can be repeated if necessary once a 5-10 minute period of cerebral reperfusion is reached. After completion of the main surgical procedure the occluding catheters 16, 20 can be pulled back into the left subclavian artery 28 for subsequent removal.

Measurement of the pressure at the occluding, balloons 18, 22 and at downstream areas from the occluding balloons 18, 22 via distal openings 42 and 56 may improve the efficacy and safety of the carotid balloon occlusion. Thus, if the post-balloon occlusion pressure measured in the innominate artery 24 and carotid artery 14 drops more than 50% after the balloons 18, 22 are inflated, the occlusion of the arteries 12, 14 is complete. On the other hand, the intra-balloon pressure during balloon 18, 22 inflation should not exceed by more than 10-20 mm Hg the patient's systemic arterial pressure in order to avoid an undue trauma to the arterial walls 24, 14. In some exemplary embodiments the pressure of the occluding balloons 18 and 22 that causes their inflation may be up to 50 mm of Hg, although in other embodiments the pressure of inflation of the occluding balloons 18 and 22 may be greater than 50 mm of Hg.

The apparatus 10 may achieve adequate bilateral carotid flow interruption at the minimal degree of internal pressure on the carotid walls 12, 14 in order to minimize potential injury to these vessels. This goal should be achieved by low-pressure inflation of the occlusion balloons 18, 22, monitoring of the proximal and post-occlusion carotid arterial pressures. This may also be accomplished by comparing systemic arterial and occluding balloon 18, 22 pressures and trying to keep pressures in occlusion balloons 18, 22 only slightly higher than systemic arterial pressure.

Placement of the first occluding balloon 18 in the right carotid artery 12 may be done so that placement is not in the innominate artery 24. This arrangement may protect the right carotid artery 12, but not the right vertebral circulation. This measure is sometimes necessary in patients with significant calcification and atherosclerotic changes of the innominate artery 24, precluding safe balloon occlusion of this vessel 24. With the left carotid artery 14 occluded by a second occluding balloon 22, this method will still provide significant cerebral protection by blocking the inflow of emboli 90 into carotid circulation bilaterally. In addition, temporary interruption of flow through both carotid arteries 12, 14 is expected to produce concomitant decrease of flow through both subclavian arteries 26, 28, thus decreasing the risk of cerebral emboli 90 via both carotid and vertebrobasilar pathways.

Figure 19:
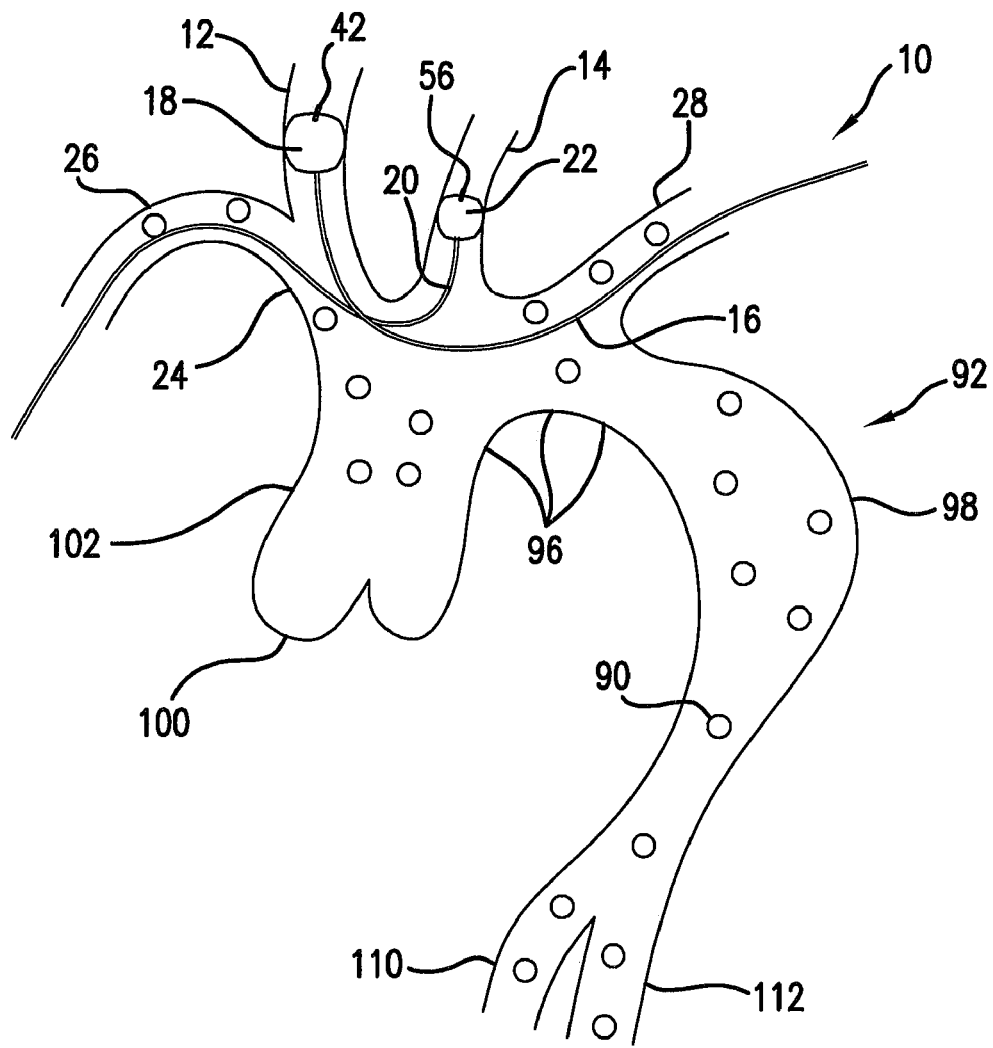
FIG. 19 is a front view of the circulatory system with two inflated occluding balloons inserted via contralateral upper extremities.

The apparatus 10 may be introduced into the circulatory system 92 in a variety of manners and it is to be understood that the disclosed embodiments are only exemplary. With reference to FIG. 19, the apparatus 10 does not include an insertion device 58. The first occluding catheter 16 is introduced through the left subclavian artery 28 and into the right carotid artery 12 where the first occluding balloon 18 may be used to occlude the right carotid artery 12. The second occluding catheter 20 may be introduced through the right subclavian artery 26 and moved into the left carotid artery 14 wherein the second occluding balloon 22 is inflated to occlude the left carotid artery 14.

Figure 20:
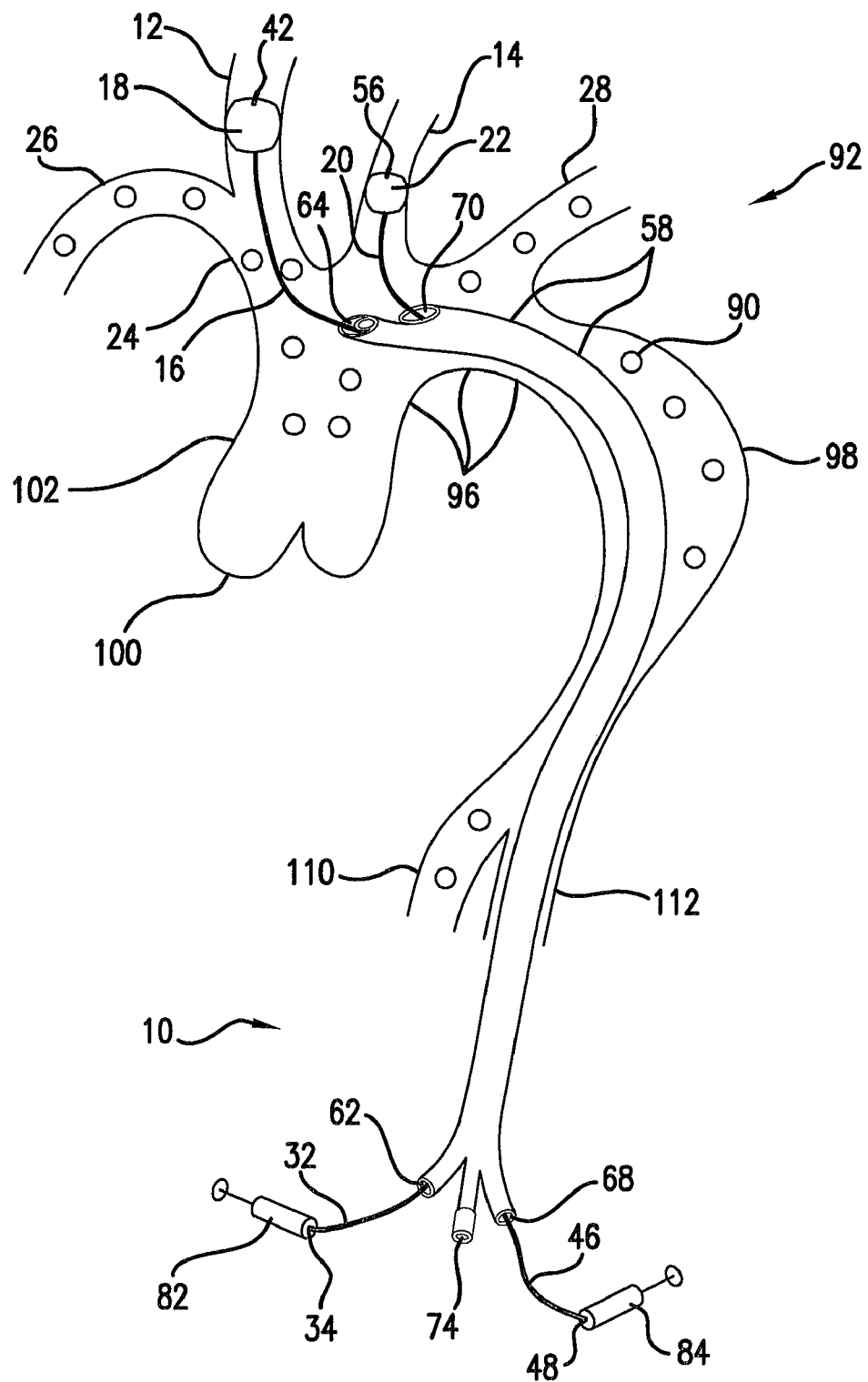
FIG. 20 is a front view of the circulatory system with the apparatus inserted via the left femoral artery.

In other arrangements, the apparatus 10 may be inserted through the right subclavian artery 26 and not located at all in the left subclavian artery 28. When this is done, the first occluding catheter 16 may be advanced into the left carotid artery 14, and the second occluding catheter 20 may be advanced into the innominate artery 24 or the right carotid artery 12. With reference to FIG. 20, the apparatus 10 may be introduced through the left femoral artery 112 and advanced into the aortic arch 96 such that no portion of the apparatus 10 is located in the right or left subclavian artery 26, 28. In this arrangement, emboli 90 may move through both the right and left subclavian arteries 26, 28.

The apparatus may thus achieve simultaneous occlusion of both carotid arteries 12, 14. However, in some arrangements one, of the occluding balloons 18 may be actuated first to occlude one of the carotid arteries 12, 14, while subsequently the other occluding balloon 22 can be actuated to occlude the other one of the carotid arteries 12, 14. The anatomy of the aortic arch 96 and the take off points of the innominate artery 24 and left carotid artery 14 can be estimated by preoperative computerized angiography and intraoperative aortography. The distal openings 64, 70 can be advanced into the aortic arch 96 to correspond anatomically to the orifices of the innominate artery 24 and the left carotid artery 14. The occluding balloons 18, 22 can be fully or partially inflated once they have exited the insertion device 58.

The occluding catheters 16 and 20 may be wireless in that they can be placed within the patient without the use of a guide wire 118. The occluding balloons 18, 22 can be arranged so that when inflated all of the blood into the artery in question (12, 14, 26, 24, and/or 28) is blocked. In this regard, no blood flows past the inflated balloons 18, 22 or the insertion device 58. The arteries 12, 14, 26, 24, and/or 28 may be completely prevented from having blood flowing through them as per the arrangement of all portions of the apparatus 10. In other arrangements, the occluding balloons 18, 22 are arranged so that some blood does flow into arteries 12, 14, 26, 24, and/or 28. The balloons 18, 22 can be partially inflated but not inflated all the way to seal the arterial wall. The balloons 18, 22 can be made so that even if fully inflated they are small enough not to completely block blood flow to seal the arterial wall. Some amount of blood can in fact flow past the inflated balloons 18, 22 and into the various arteries 12, 14, 26, 24, and/or 28. The blood that flows past is unfiltered blood. Although emboli 90 may still flow into cerebral circulation and cause stroke, even partial reduction of flow will cause a partial reduction in the chance of stroke or the severity of stroke. The apparatus 10 may block from 30%-50%, from 50%-70%, from 70%-90% or up to 100% of the blood flow into the various arteries 12, 14, 26, 24, and/or 28 in accordance with certain exemplary embodiments. Blood that does flow into the various arteries 12, 14, 26, 24, and/or 28 comes directly from the aortic arch 96 and is unfiltered. As used herein, the term "occlude" is broad enough to include complete blockage of blood flow and to include partial blockage of blood flow while still allowing some unfiltered blood to flow through. Also, as used herein when referring to a "block" of blood flow, it is to be understood that this term is broad enough to cover complete blocking of blood flow and partial blocking of blood flow such that some amount of unfiltered blood flows through.

In use, the occluding catheters 16, 20 may be used so that partial inflation or total inflation of the occluding balloons 18, 22 is made during, a medical procedure to control the blood flow through by reducing the risk of stroke while still allowing blood to enter the cerebral circulation. When fully inflated to completely block blood flow, the occluding balloons 18, 22 are solid components and not filters and do not filter emboli 90 but, rather prevent everything including blood and emboli 90 from moving therethrough. The occluding balloons 18, 22 may completely block blood and emboli 90 from moving through the particular blood vessel such that no blood or emboli 90 flows through the tube sections of the occluding catheters 16, 20 past the occluding balloons 18, 22. The occluding balloons 18, 22 and the tubular sections of the occluding catheters 16, 20 located at the blocked area of blood/emboli 90 flow when positioned are not porous members and do not filter any blood. However, when the occluding balloons 18, 22 are deflated, partially deflated, or fully inflated but less than the diameter of the vessel they are in allow blood and emboli 90 to flow around them through the particular blood vessel and they are not filtered in any manner, although the flow rate may be decreased due to the presence of the occluding balloons 18, 22 and tubular sections of the occluding catheters 16, 20.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. An apparatus for preventing stroke by occluding blood flow through a right carotid artery and a left carotid artery of a patient, comprising:
   an insertion device that defines a first occluding catheter channel and a second occluding catheter channel;
   a first occluding catheter that carries a first occluding balloon that has an inflated configuration that occludes either the right carotid artery or the left carotid artery, the first occluding catheter configured to be movable within the first occluding catheter channel; and
   a second occluding catheter that carries a second occluding balloon that has an inflated configuration that occludes the other one of the right carotid artery or the left carotid artery that is not occluded by the first occluding balloon, the second occluding catheter configured to be movable within the second occluding catheter channel;
   wherein the first occluding catheter has a first occluding catheter shaft, wherein a first inflation channel is defined by the first occluding catheter shaft, wherein the first inflation channel extends from a first proximal inflation port to a first occluding balloon opening, wherein the first occluding catheter shaft defines a first pressure measurement channel that extends from a first proximal measurement port to a first distal opening;
   wherein the second occluding catheter has a second occluding catheter shaft, wherein a second inflation channel is defined by the second occluding catheter shaft, wherein the second inflation channel extends from a second proximal inflation port to a second occluding balloon opening, wherein the second occluding catheter shaft defines a second pressure measurement channel that extends from a second proximal measurement port to a second distal opening;
   wherein the insertion device has a first proximal opening from which the first occluding catheter channel extends to a first distal opening of the insertion device, wherein the insertion device has a second proximal opening from which the second occluding catheter channel extends to a second distal opening of the insertion device; and
   wherein the first occluding catheter channel ends in an insertion device first distal opening, wherein the second occluding catheter channel ends in an insertion device second distal opening, wherein the orientations and positions of the insertion device first distal opening and the insertion device second distal opening specifically correspond to the locations and orifices of an innominate artery and the left carotid artery correlating with an average distance between these two orifices ranging from 0.5 centimeters to 5.0 centimeters for direct catheterization and occlusion of the innominate artery and the left carotid artery, wherein both the insertion device first distal opening and the insertion device second distal opening are located on the same side of the insertion device and both are configured to directly face the orifices of the innominate artery and the left carotid artery.

2. The apparatus as set forth in claim 1, wherein the first occluding balloon is in the inflated configuration and is located in an innominate artery of the patient and occludes flow to the right carotid artery and a right subclavian artery of the patient, wherein the second occluding balloon is in the inflated configuration and is located in the left carotid artery and occludes the left carotid artery.

3. The apparatus as set forth in claim 1, wherein the first occluding balloon is in the inflated configuration and is located in the right carotid artery and occludes the right carotid artery and does not occlude a right subclavian artery of the patient, and wherein the second occluding balloon is in the inflated configuration and is located in the left carotid artery and occludes the left carotid artery.

4. The apparatus as set forth in claim 1, wherein the insertion device defines a pressure measurement channel that extends from a pressure measurement proximal opening to a pressure measurement distal opening, wherein the pressure measurement channel is not in fluid communication with the first occluding catheter channel and is not in fluid communication with the second occluding catheter channel.

5. The apparatus as set forth in claim 1, wherein the first occluding balloon is in the inflated configuration and wherein the second occluding balloon is in the inflated configuration, wherein the first occluding balloon has a first diameter and wherein the second occluding balloon has a second diameter, and wherein the first diameter is from 50%-100% larger than the second diameter.

6. The apparatus as set forth in claim 1, wherein the first occluding catheter and the first occluding balloon are made of a highly compliant material and have a floating capability to reach desired positions in the circulatory system of the patient by being propelled with forward arterial blood flow of the circulatory system;
   wherein the second occluding catheter and the second occluding balloon are made of a highly compliant material and have a floating capability to reach desired positions in the circulatory system of the patient by being propelled with forward arterial blood flow of the circulatory system;
   wherein the first occluding catheter and the first occluding balloon and the second occluding catheter and the second occluding balloon are positioned without and do not have a guide wire.

7. The apparatus as set forth in claim 1, further comprising an alarm system that activates a pressure supply to the first occluding balloon and the second occluding balloon to inflate the first occluding balloon and the second occluding balloon to the inflated configurations when microemboli are detected, wherein the alarm system deflates the first and second occluding balloons from the inflated configurations when the first and second occluding balloons have remained in the inflated configurations for a cut-off period of time, and wherein the alarm system has a manual override to prevent inflation and deflation by the alarm system.

8. The apparatus as set forth in claim 1, wherein the first occluding balloon is in the inflated configuration and completely blocks blood flow through either the right carotid artery or the left carotid artery; and
   wherein the second occluding balloon is in the inflated configuration and completely blocks blood flow through the other one of the right carotid artery or the left carotid artery that is not occluded by the first occluding balloon.

9. The apparatus as set forth in claim 1, wherein the first occluding balloon blocks from 30%-100% of the blood flowing through the artery that the first occluding balloon occludes; and wherein the second occluding balloon blocks from 30%-100% of the blood flowing through the artery that the second occluding balloon occludes.

10. The apparatus as set forth in claim 1, further comprising an alarm system that deflates the first and second occluding balloons from the inflated configurations when the first and second occluding balloons have remained in the inflated configurations for a cut-off period of time.

11. An apparatus for preventing stroke by occluding blood flow through a right carotid artery and a left carotid artery of a patient, comprising:
- an insertion device that defines a first occluding catheter channel and a second occluding catheter channel;
- a first occluding catheter that carries a first occluding balloon that has an inflated configuration that occludes either the right carotid artery or the left carotid artery, wherein the first occluding catheter is located in the first occluding catheter channel and is movable through the first occluding catheter channel such that the first occluding catheter is movable relative to the insertion device; and
- a second occluding catheter that carries a second occluding balloon that has an inflated configuration that occludes the other one of the right carotid artery or the left carotid artery that is not occluded by the first occluding balloon, wherein the second occluding catheter is located in the second occluding catheter channel and is movable through the second occluding catheter channel such that the second occluding catheter is movable relative to the insertion device and is movable relative to the first occluding catheter;
- wherein the first occluding catheter has a first occluding catheter shaft, wherein a first inflation channel is defined by the first occluding catheter shaft, wherein the first inflation channel extends from a first proximal inflation port to a first occluding balloon opening, wherein the first occluding catheter shaft defines a first pressure measurement channel that extends from a first proximal measurement port to a first distal opening;
- wherein the second occluding catheter has a second occluding catheter shaft, wherein a second inflation channel is defined by the second occluding catheter shaft, wherein the second inflation channel extends from a second proximal inflation port to a second occluding balloon opening, wherein the second occluding catheter shaft defines a second pressure measurement channel that extends from a second proximal measurement port to a second distal opening;
- wherein the insertion device has a first proximal opening from which the first occluding catheter channel extends to a first distal opening of the insertion device, wherein the insertion device has a second proximal opening from which the second occluding catheter channel extends to a second distal opening of the insertion device; and
- wherein the first occluding catheter channel ends in an insertion device first distal opening, wherein the second occluding catheter channel ends in an insertion device second distal opening, wherein the orientations and positions of the insertion device first distal opening and the insertion device second distal opening specifically correspond to the locations and orifices of an innominate artery and the left carotid artery correlating with an average distance between these two orifices ranging from 0.5 centimeters to 5.0 centimeters for direct catheterization and occlusion of the innominate artery and the left carotid artery, wherein both the insertion device first distal opening and the insertion device second distal opening are located on the same side of the insertion device and both are configured to directly face the orifices of the innominate artery and the left carotid artery.

12. The apparatus as set forth in claim 11, wherein the insertion device defines a pressure measurement channel that extends from a pressure measurement proximal opening to a pressure measurement distal opening, wherein the pressure measurement channel is not in fluid communication with the first occluding catheter channel and is not in fluid communication with the second occluding catheter channel;
- wherein the first occluding balloon is located outside of the insertion device and is in the inflated configuration and completely blocks blood flow through the right carotid artery, wherein the second occluding balloon is located outside of the insertion device and is in the inflated configuration and completely blocks blood flow through the left carotid artery.

13. The apparatus as set forth in claim 11, wherein the first occluding balloon blocks from 30%-100% of the blood flowing through the artery that the first occluding balloon occludes; and wherein the second occluding balloon blocks from 30%-100% of the blood flowing through the artery that the second occluding balloon occludes.

14. A system for preventing stroke by occluding blood flow through a right carotid artery and a left carotid artery of a patient, comprising:
- an insertion device that defines a first occluding catheter channel and a second occluding catheter channel;
- a first occluding catheter that carries a first occluding balloon that has an inflated configuration that occludes the flow to either the right carotid artery or the left carotid artery, the first occluding catheter configured to be movable within the first occluding catheter channel;
- a second occluding catheter that carries a second occluding balloon that has an inflated configuration that occludes the flow to the other one of the right carotid artery or the left carotid artery that is not occluded by the first occluding balloon, the second occluding catheter configured to be movable within the second occluding catheter channel;
- a detector selected from the group consisting of angiography, echocardiography, carotid Doppler, arterial pressure and waveform patterns, percutaneous cerebral oximetery, electroencephalography, and transcranial Doppler that detects the presence of emboli; and
- an alarm system that initiates inflation of the first and second occluding balloons when the detector detects the emboli;
- wherein the first occluding catheter has a first occluding catheter shaft, wherein a first inflation channel is defined by the first occluding catheter shaft, wherein the first inflation channel extends from a first proximal inflation port to a first occluding balloon opening, wherein the first occluding catheter shaft defines a first pressure measurement channel that extends from a first proximal measurement port to a first distal opening;
- wherein the second occluding catheter has a second occluding catheter shaft, wherein a second inflation channel is defined by the second occluding catheter shaft, wherein the second inflation channel extends from a second proximal inflation port to a second occluding balloon opening, wherein the second occluding catheter shaft defines a second pressure measurement channel that extends from a second proximal measurement port to a second distal opening;
- wherein the insertion device has a first proximal opening from which the first occluding catheter channel extends to a first distal opening of the insertion device, wherein the insertion device has a second proximal opening from which the second occluding catheter channel extends to a second distal opening of the insertion device; and wherein the first occluding catheter channel ends in an insertion device first distal opening, wherein the second occluding catheter channel ends in an insertion device second distal opening, wherein the orientations and positions of the insertion device first distal opening and the insertion device second distal opening specifically correspond to the locations and orifices of an innominate artery and the left carotid artery correlating with an average distance between these two orifices ranging from 0.5 centimeters to 5.0 centimeters for direct catheterization and occlusion of the innominate artery and the left carotid artery, wherein both the insertion device first distal opening and the insertion device second distal opening are located on the same side of the insertion device and both are configured to directly face the orifices of the innominate artery and the left carotid artery.

\* \* \* \* \*